United States Patent [19]

Andersson et al.

[11] Patent Number: 5,326,695
[45] Date of Patent: Jul. 5, 1994

[54] PLATELET DERIVED GROWTH FACTOR AGONISTS

[75] Inventors: Maria Andersson; Gudrun Backstrom; Ulla Engström; Carl-Henrik Heldin; Ulf Hellman; Arne Östman; Bengt Westermark, all of Uppsala, Sweden

[73] Assignee: Ludwig Institute for Cancer Research, New York, N.Y.

[21] Appl. No.: 883,949

[22] Filed: May 15, 1992

[51] Int. Cl.$^5$ .................. C12N 5/00; C12N 15/00; C12P 21/00
[52] U.S. Cl. .................. 435/70.1; 435/244; 435/243; 435/240.1; 435/320.1; 536/23.5; 536/23.51; 530/350; 530/399
[58] Field of Search .......... 435/69.1, 69.4, 70.1, 435/172.3, 240.1, 320.1, 252.33, 240.2, 252.3, 255, 256, 243, 244; 536/23.5, 23.51; 514/12; 530/350, 399

[56] References Cited

U.S. PATENT DOCUMENTS

| | | | |
|---|---|---|---|
| 4,845,075 | 7/1989 | Murray et al. | 514/12 |
| 4,889,919 | 12/1989 | Murray et al. | 530/351 |
| 4,959,314 | 9/1990 | Mark et al. | 435/69.1 |
| 5,128,321 | 7/1992 | Murray et al. | 514/12 |
| 5,132,408 | 7/1992 | Baird et al. | 530/399 |
| 5,149,691 | 9/1992 | Rutherford | 514/12 |

FOREIGN PATENT DOCUMENTS 0288307 10/1988 European Pat. Off. .
WO9014425 11/1990 PCT Int'l Appl. .

OTHER PUBLICATIONS

Claesson-Welsh, *PNAS*, 86:4917-21, 1989.
Betsholtz, C. et al., *Nature*, 320:695-699, 1986.
Heldin et al., Cell Reg. 1: 555-566 (Jul. 1990).
Ostman et al., J. Biol. Chem. 263: 16202-16208 (1988).
Truett et al., DNA (4(5): 333-349 (1985).
Ostman et al., *Cell Regul.* 2:503-512, 1991.

Primary Examiner—Robert J. Hill, Jr.
Assistant Examiner—Marianne Porta Allen
Attorney, Agent, or Firm—Felfe & Lynch

[57] ABSTRACT

The invention described PDGF modifiers. These are peptides which are derived from wild type PDGF monomers, and function as either agonists or antagonists. Various uses of these are described, as well as recombinant means of production. PDGF-B agonists comprising amino acids 97-180 of the PDGF-B monomer having the cysteines at amino acid residues 124 and 133 substituted, nucleic acid molecules encoding the agonists, plasmids, transformed host cells, and methods for causing receptor dimerization and autophosphorylation in a cell having PDGF-$\beta$ receptors

FIG. 7B

```
SIEEAVPAVCKTRTVIYEIPRSQVDPTSANFLIWP
   sp4-----@--------
            sp3-----------------------------
PCVEVKRCTGCCNTSSVKCQPSRVHHRSVKVAKVE
   sp1---@--#@------@-------
-#--
YVRKKPKLKEVQVRLEEHLECACATTSLNPDYREE
              sp2@-@-----------

DTGRPRESGKKRKRKRLKPT
```

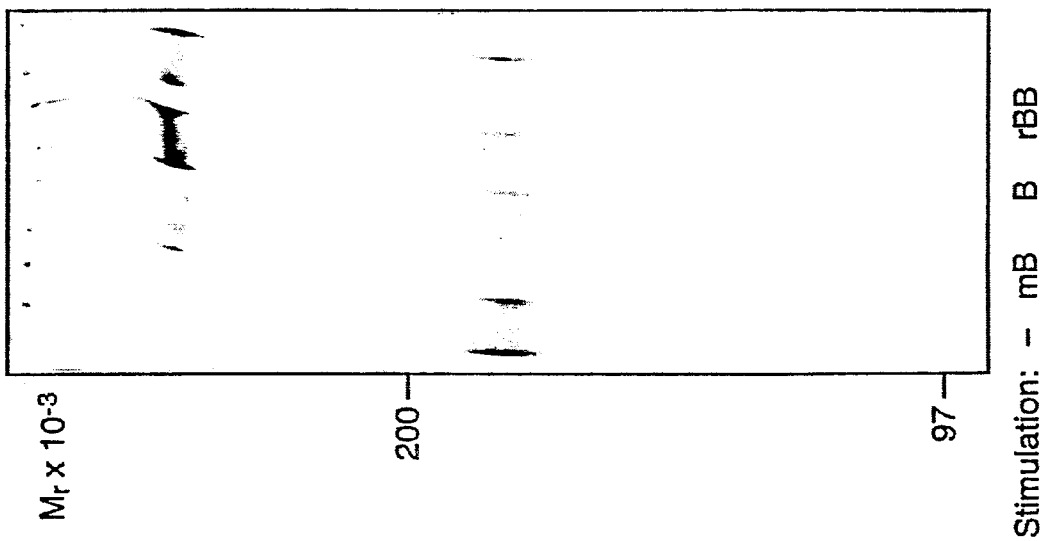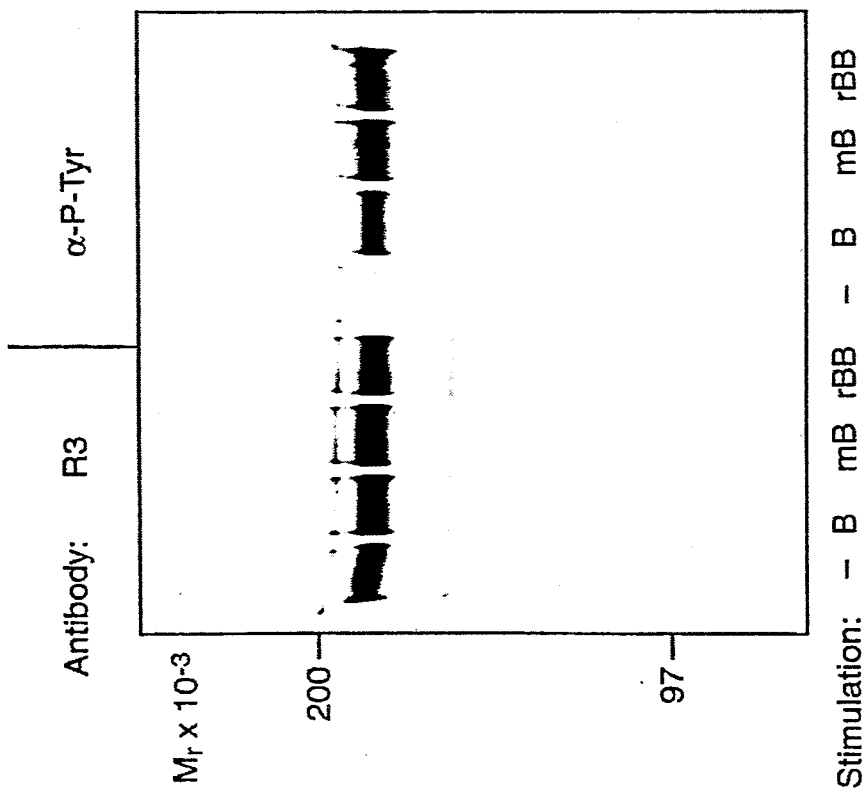

PLATELET DERIVED GROWTH FACTOR AGONISTS

FIELD OF THE INVENTION

This invention relates to agonists and antagonists of the molecule known as platelet derived growth factor, or "PDGF". More particularly, it relates to peptides and monomers, some of which have agonistic or antagonistic effect in connection with their binding to the α and β receptors for PDGF. Also described are novel heterodimers useful in various ways typical of proteins.

BACKGROUND AND PRIOR ART

PDGF was first recognized as a component of platelet α granules, which had growth promoting activity for smooth muscle cells and fibroblasts (Heldin and Westermark, Cell Regul 1: 555-566 (7-90)). It has also been implicated in the stimulation of connective tissue-derived cells in vitro (Östman et al., J. Biol. Chem. 263(31): 16202-16208 (11-88)), as the major mitogenic protein for mesenchymal cells (Murray et al., U.S. Pat. Nos. 4,889,919 and 4,845,075), and as an inducer of cell multiplication and DNA synthesis in cultured muscle cells, fibroblasts and glial cells (Kelly et al, PCT Application WO90/14425 (Nov. 29, 1990)). It has also been shown to be involved in the wound healing response (Ross et al., N. Eng. J. Med. 295: 369 (1976)), and may be involved in a causative role for the development of proliferative lesions of artherosclerosis (Ross) supra. Others have suggested that this molecule may be a mediator of tumor development as well as in nonmalignant proliferative disorders (Heldin et al., supra).

The PDGF molecule has been very well characterized. It is known to exist as a heterodimer of an "A" chain and a "B" chain, connected to each other via disulphide bonds. The dimer, sometimes referred to as "PDGF-AB", has a molecular mass of about 30 KDa. Amino acid sequences are known for both the A and B chains, as shown, e.g., by Murray et al., U.S. Pat. Nos. 4,889,919 and 4,845,075, the disclosures of which are incorporated by reference. The mature chains contain slightly more than 100 amino acids, and are about 60% homologous. Heldin et al., supra.

Dimers PDGF-AA and PDGF-BB have been produced via recombinant means, and have also been isolated from natural sources (see Murray et al., supra; Heldin et al., supra). The various dimers, or "isoforms" differ in functional properties and secretory behavior.

The mechanism by which PDGF acts on cells has received intensive scrutiny, and it has been established that there are two receptors for PDGF, the "α" and "β" receptors. The α receptor binds all isoforms, whereas β receptor does not bind PDGF-AA, binds PDGF-AB with low affinity, and PDGF-BB with high affinity (Heldin et al., supra; Östman et al., supra). The receptor is synthesized as a 140 KDa precursor protein which matures to one of 170 KDa, and the β receptor is recognized as a precursor of 160 KDa, and a mature molecule of 180 KDa. cDNA for both receptors has also been isolated (Heldin et al., supra; Kelly et al., supra).

The structure of the receptors is linked to their function; both comprise five immunoglobulin like domains (extracellular portion), and intracellular portions containing protein tyrosine kinase domains with characteristic insert sequences which have no homology to kinase domains (Yarden et al., Nature 323: 226-232 (1986); Matsui et al., Science 243: 800-803 (1989); Claesson-Welsh et al., PNAS 86: 4917-4921 (1989). When PDGF binds to these receptors, dimerization of the receptor molecules is induced, followed by kinase activation and autophosphorylation of the receptors (Heldin et al., J. Biol. Chem. 264: 8905-8912 (1989); Seifert et al., J. Biol. Chem. 264: 8771-8778 (1989); Bishayee et al., J. Biol. Chem. 264: 11699-11705 (1989)).

The many mechanisms with which PDGF is involved and the manner in which it reacts with its receptors suggests further study as to how this interaction can be modified One approach to this type of study involves the use of agonists and antagonists. The molecules, using the definitions employed by Kelly et al., supra, either mimic the effect of PDGF (agonists), or block the interaction of receptor and ligand (antagonists).

The art has long recognized that agonists and antagonists for various materials exist, and Kelly et al., via their discussion, de facto assumes that these exist for PDGF. Review of the literature indicates, however, that no proteinaceous agonists and antagonists to PDGF are taught. For the reasons described supra, it would be desirable to have such material available.

The two patents to Murray et all, cited supra discuss potential amino acid substitution of cysteine residues in the monomeric chains, provided that these substitutions do not destroy the biological activity of the molecules. The '919 patent generally teaches modifications of PDGF AA molecules. Neither reference teaches that modified dimers of PDGF have antagonistic activity against wild type PDGF.

It has now been found that portions of the PDGF chains, i.e., peptides derived therefrom, can be used as both agonists and antagonists. It has also been found that manipulation of the dimeric structure of the PDGF molecule leads to the creation of monomeric molecules which are PDGF agonists. Additionally, it has been found that in dimeric PDGF molecules, there is a "cross" bond of the second cysteine of each monomer with the fourth cysteine of the other monomer, and that elimination of one of these bond creates a dimeric molecule which competes with wild type PDGF. PDGF-B agonists comprising amino acids 97-180 of the PDGF-B monomer having the cysteines at amino acid residues 124 and 133 substituted, nucleic acid molecules encoding the agonists, plasmids, transformed host cells, and methods for causing receptor dimerization and autophosphorylation in a cell having PDGF-β receptors on its surface comprising administering the PDGF-B agonist form part of the invention. Also described are new PDGF heterodimers, methods and systems for producing these. These are the key features of the invention described herein, which will be seen from the disclosure which follows.

BRIEF DESCRIPTION OF THE FIGURES

FIG. 7B sets forth amino acid sequences for the peptides eluted from the HPLC experiments of FIG. 7A and the sequence for PDGF-B referred to infra and in Betsholtz et al., Nature 320: 695-699 (1986), and presented at SEQ ID NO: 7.

FIGS. 10A and 10B show SDS-PAGE immunoprecipitation studies using PDGF B derivatives (10A) and the effect of derivatives on dimerization (10B).

DETAILED DESCRIPTION OF PREFERRED EMBODIMENTS

Examples 1

Figure 1:
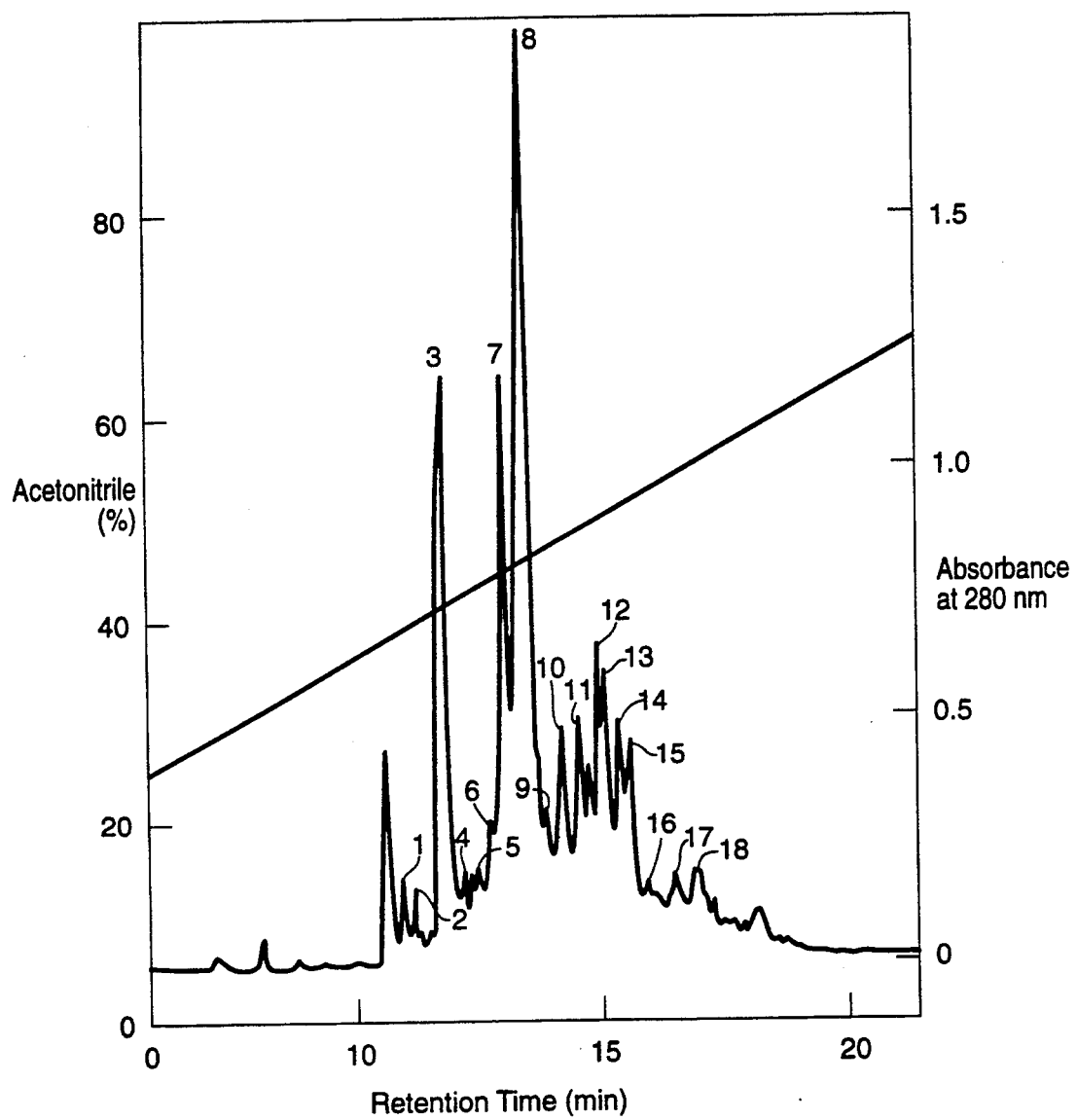
FIG. 1 shows HPLC purification of peptide 16T, which is elaborated upon in the examples.

In order to test for receptor binding, cultures of human foreskin fibroblast cell line AG1518 (obtained from the Human Mutant Cell Repository), were grown to confluence in Ham's F-12 medium containing 10% newborn calf serum. Those cells which were to be used in analysis of PDGF-β receptor binding were preincubated for 60 minutes at 37° C. in 0.5 ml/well of Ham's F-12 medium, supplemented with 1 mg/ml of bovine serum albumin (BSA), and 50 ng/ml of PDGF-AA. This combination down regulates PDGF-α receptor, as per Claesson-Welsh et al., J. Biol. Chem. 264: 1742-1747 (1989).

Cells were prepared for receptor binding analyses by washing with ice cold binding buffer (phosphate buffered saline with 0.9 mM CaCl$_2$, 0.49 mM MgSO$_4$ and 1 mg/ml BSA). The cells were then incubated on ice for 90 minutes with different concentrations (0-100 ug/ml) of synthetic peptides (listed in Table 1, infra), in 0.5 ml of binding buffer per well. This was followed by addition of $^{125}$I labelled PDGF-AA, PDGF-BB, or EGF. The PDGF dimers showed about 50,000 cpm per well, and the EGF about 100,000 cpm per well. The labelled ligand was added and then incubated for 60 minutes at 0° C., after which the cells were washed five times with ice cold binding buffer. The washed cells were then lysed for 60 minutes at room temperature in a lysis buffer (1% Triton X-100, 10% glycerol, 20 mM Tris-HCl, pH 7.5). Solubilized radioactivity was determined in a gamma counter. Competing activities of synthetic peptides were compared to standard curves, using unlabelled ligand.

The peptides used were all derived from the amino acid sequence of the PDGF-B chains. Amino acid designations are in accordance with those provided by Betsholtz et al., Nature 320: 695-699 (1986), the disclosure of which is incorporated by reference. This paper gives the complete, unprocessed sequence for both the A chain and the B chain of PDGF. It is to be understood that when numbering is used herein (e.g., "Cys 123"), this refers to the complete, unprocessed sequence of the monomer; however when position is used to describe the placement of cysteine groups, e.g., "second cysteine", this refers to the processed molecule. The first amino acid in the processed PDGF A chain is serine, and is found at position 87 of the unprocessed molecule. The first amino acid in PDGF-B chain is also serine, and is found at position 82 of the unprocessed chain. Unprocessed PDGF A is 211 amino acids long; unprocessed PDGF B is 241 amino acids long.

TABLE 1

| | Synthesis Peptides |
|---|---|
| Peptide Number | Portion of PDGF-B amino acid sequence |
| 1 | 155-180, but Cys at 178 changed to Ser |
| 2 | 141-163 |
| 3 | 142-163 |
| 4 | 142-179 |
| 5 | 111-140, but Cys at 124, 133 and 134 changed to Ser |
| 6 | 116-127 |
| 7 | 116-127 and 147-163 |
| 8 | 121-127 and 147-163 |
| 9 | 116-127 and 147-157 |
| 10 | 116-127 and 147-163 |
| 11 | 116-127 and 152-163 |
| 12 | 116-123 and 153-161 |
| 13 | 116-123 and 153-161 |
| 14 | 116-121 and 153-162 |
| 15 | 116-119 and 154-162 |
| 16 | 116-121 and 157-163 |
| 17 | 107-127 and 152-167 |
| 18 | 98-106 and 116-127 and 152-163 |
| *19T | 112-121 and 157-163 |
| *16 | 116-121 and 157-163 |
| *16T | 116-121 and 157-163 but tryptophan is changed to thioanisole |
| *16NPS | 116-121 and 157-163, but tryptophan is modified by nitrophenyl sulfonyl |
| *20 | Glu Ala Phe Ile Lys Trp Leu Val Arg Asn Lys Val Pro |
| *20T | Glu Ala Phe Ile Lys Trp Leu Val Arg Asn Lys Val Pro, but tryptophan is modified by thioanisole |

In Table 1, an asterisk means homogeneous peptide was used. Otherwise, crude peptide was used. An explanation of homogeneous and crude peptide is presented infra.

The ability of the peptides to inhibit binding of PDGF-BB was measured in terms of how much peptide was needed to decrease binding by 50%. In Table 2, "+++" means <30 μm; "++" from 30-60 μm; "+" 60-150 μm; and "−", >150 μm.

TABLE 2

| Ability to Compete With PDGF-BB For Binding | |
|---|---|
| Peptide | Inhibitory Activity |
| 1 | − |
| 2 | − |
| 3 | − |
| 4 | ++ |
| 5 | + |
| 6 | + |
| 7 | +++ |
| 8 | − |
| 9 | +++ |

TABLE 2-continued

| Ability to Compete With PDGF-BB For Binding | |
|---|---|
| Peptide | Inhibitory Activity |
| 10 | +++ |
| 11 | +++ |
| 12 | + |
| 13 | + |
| 14 | + |
| 15 | − |
| 16 | +++ |
| 17 | +++ |
| 18 | +++ |
| *19T | +++ |
| *16 | − |
| *16T | +++ |
| *16NPS | +++ |
| *20 | − |
| *20T | − |

While only results for PDGF-BB inhibition are shown, similar results were obtained when PDGF-AA was used.

The peptides tested were all derived from the region spanning amino acids 97–180 ("Cys-Cys") of PDGF-B, because this region has been found to be sufficient to impart full biological activity of the molecule. (King et al., Proc. Natl. Acad. Sci. USA 82: 5295–5299 (1985)).

Co-linear peptides 1–6 all yielded only limited inhibition. The weak inhibition secured with peptides 4 and 5 suggested that combination of two regions of the sequence might be more effective, since peptides 4 and 5 were obtained from C terminal and N terminal regions, respectively.

Peptide 7, 29 amino acids long and containing 12 N-terminal region and 17 C-terminal amino acids, competed efficiently for both receptors, with 50% competition at abut 6 µM. In view of these results, additional peptides were prepared and tested so as to narrow the epitopes involved. Peptide 8, in which the five most N-terminal amino acids of peptide 7 were deleted, was nearly devoid of activity, as was peptide 9, lacking the six most C-terminal amino acids. When three amino acids at the N-terminal side of the epitopic junction were removed (peptide 10), or five C-terminal amino acids were removed (peptide 11), the effect on activity was lessened.

Attempts to further narrow the two epitopes led to the generation of peptide 16, which has amino acid sequence

ANFLVWEIVRKKP and maintained most of the receptor competing activity. Removal of two junction amino acids, however, yielded an insoluble peptide which could not be analyzed.

Extensions at the N-terminal (peptides 17–19), did not increase activity. The conclusion reached from this experiment is that a shortened peptide, 13 amino acids long and containing portions of two regions of B chain of PDGF is an efficient antagonist of PDGF-AA and PDGF-BB with respect to binding their $\alpha$ and $\beta$ receptors.

Example 2

The peptides used in the experiments of Example 1 had been prepared using t-Boc chemistry using a peptide synthesizer. They were cleaved from polymeric supports via incubation with HF at 0° C. for 60 minutes with 8% anisole and 4% methyl ethylsulfide as scavengers. Where peptides contained tryptophan, 3% thioanisole was added. These preparations were crude formulations.

The interesting results secured with peptide 16 suggested experiments using purified material. To that end, peptide 16 was purified via reversed phase HPLC on a Vydac C18 column (10×250 mm) using a 30 minutes gradient of 10–90% acetonitrile in 0.1% trifluoroacetic acid. Peptide was identified and analyzed using $^{252}$Cf plasma desorption mass spectrometry, as per Sundqvist et al., Mass Spectrometry Rev. 4: 421–460 (1985). Each fraction from the HPLC was then analyzed, both via the methodology described supra, and via mass spectrometry.

Figure 2:
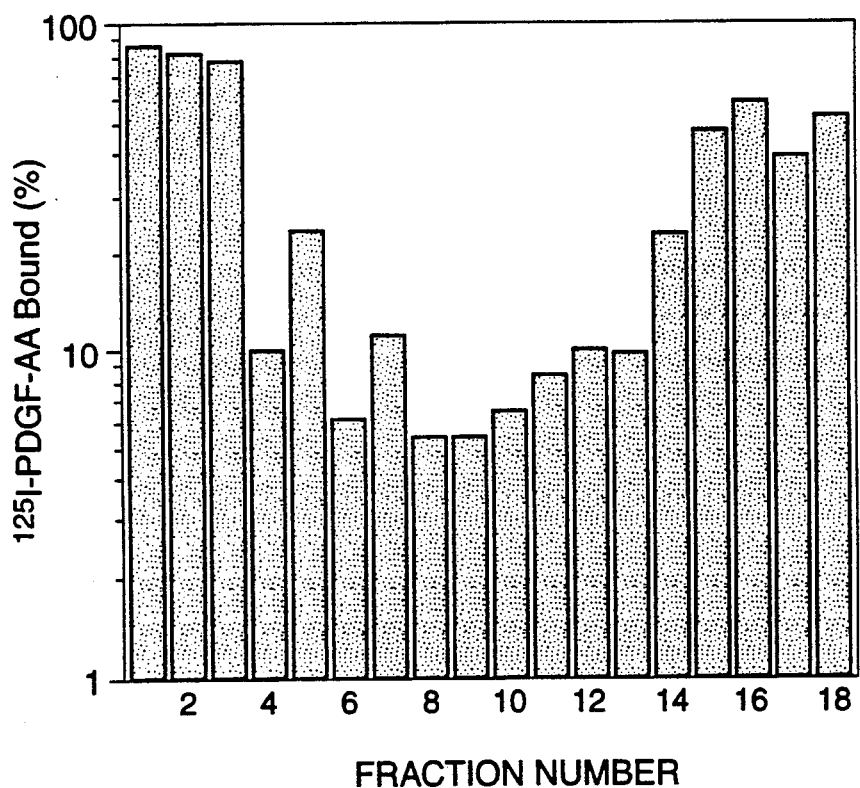
FIG. 2 shows competitor activity of peptides on $^{125}$I-PDGF-AA binding to α receptors.

Surprisingly, the component with the expected molecular mass of peptide 16 ("16*" in Tables 1 and 2), had very low activity compared to other HPLC components. A component showing a molecular mass of 122 Da, which is greater than that of peptide 16, showed higher activity Analysis of the HPLC work led to the conclusion that thioanisole had been attached to tryptophan in peptide 16 during mass spectrometry. To secure larger amounts of this peptide, referred to as "16T", higher concentrations of thioanisole were used in the deprotection step. HPLC purification is shown in FIG. 1, and the competitor activity of the various HPLC fractions are shown in FIG. 2. Table 3, which follows, presents proposed structures and masses of ions determined by HPLC.

TABLE 3

Mass spectrometric analysis of fractions collected during HPLC purification (FIG. 2B) of Peptide 16.

| Fraction | Observed m/z | Proposed molecule (Expected value of m/z within parentheses) |
|---|---|---|
| 1 | 1452.6 | M—PHE (1453.7) |
|  | 1581.6 | M Nitril (1582.9) |
| 2 | 1601.0 | M (1600.9) |
|  | 1581.5 | M Nitril (1582.9) |
| 3 | 1599.2 | M (1600.9) |
| 4 | 1485.8 | M—Asn (1486.8) |
|  | 1599.2 | M (1600.9) |
|  | 1644.9 |  |
| 5 | 1644.8 |  |
|  | 1560.0 |  |
| 6 | 1574.0 | M122-Phe (1575.9) |
|  | 1654.9 | M + tBu (1657.0) |
| 7 | 1708.1 | M122 Nitril (1705.8) |
| 8 | 1721.2 | M122 (1723.1) |
| 9 | 1754.0 | M + Tos (1755.1) |
|  | 1722.8 | M122 (1723.1) |
|  | 1689.9 | M + OBzl (1691.0) |
|  | 1651.1 | M122 - Ala (1652.0) |
|  | 1594.2 | M1222 - Lys/Glu (1594.1/1593.9) |
| 10 | 1724.7 | M122 (1723.1) |
|  | 1608.5 | M122 - Asn (1609.0) |
| 11 | 1763.9 | M122 Nitril + tBu (1761.2) |
| 12 | 1778.1 | M122 + tBu (1779.2) |
| 13 | 1778.1 | M122 + tBu (1779.2) |
| 14 | 1846.9 | M122 + Clz (1847.6) |
|  | 1875.8 | M122 + Tos (1877.3) |
| 15 | 1847.0 | M122 + Clz (1847.6) |

Abbreviations: M, Peptide 16; M122, Peptide 16T; Nitril, dehydrated asparagine; tBu, tert-Butyl; Tos, 4-toluendesulfonyl; Obzl, Benzyl ester; Cl-z, 2-chlorobenzyloxycarbonyl.

Example 3

To test the hypothesis that modification of tryptophan would potentiate activity, peptide 16 was incubated with 2-nitrophenylsulfenyl chloride (NPS-Cl), which is known to react with tryptophan (see Scoffone et al., Biochem. 7: 971–979 (1968)). The resulting derivative "16NPS", also had increased activity as an antagonist as compared to peptide 16.

Figure 3A:
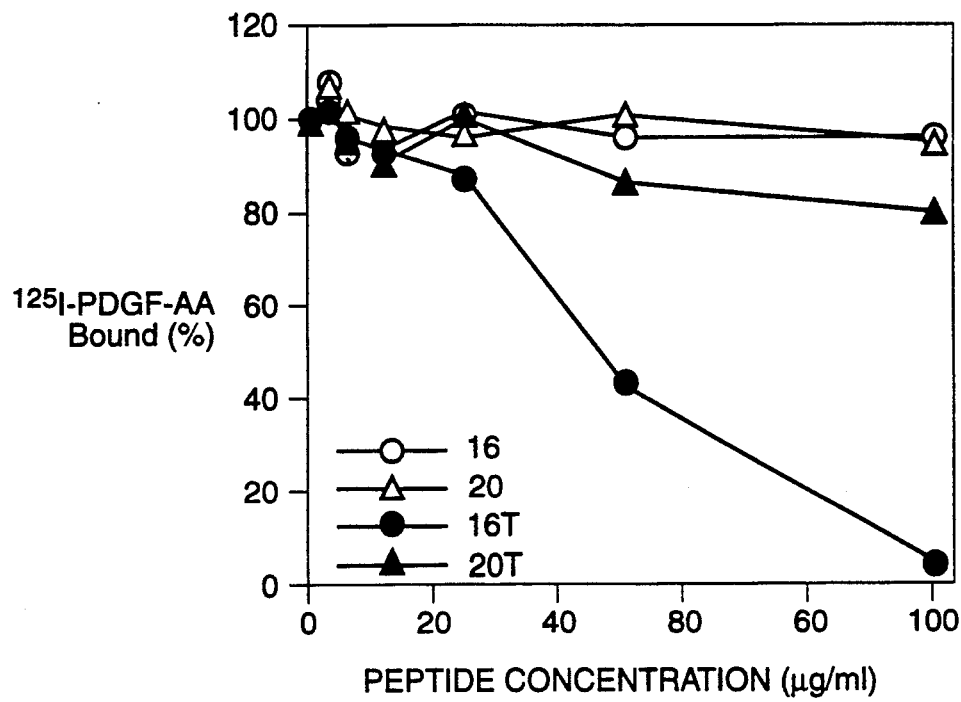
FIGS. 3A, 3B and 3C depicts competitive activity of various HPLC purified PDGF derived peptides on binding of various ligands to PDGF receptors.
Figure 3B:
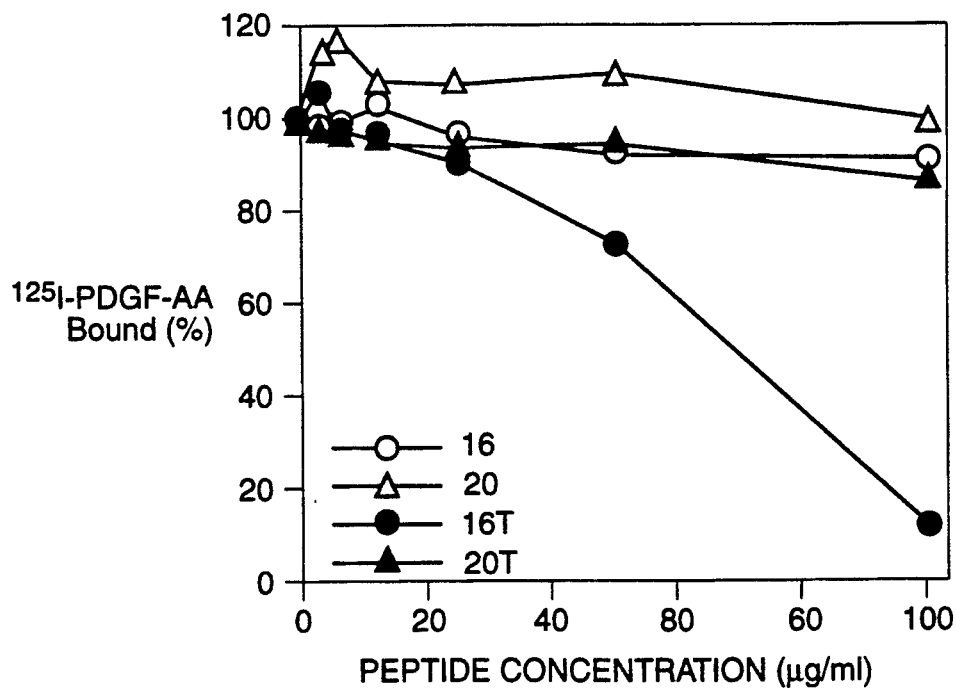
Figure 3C:
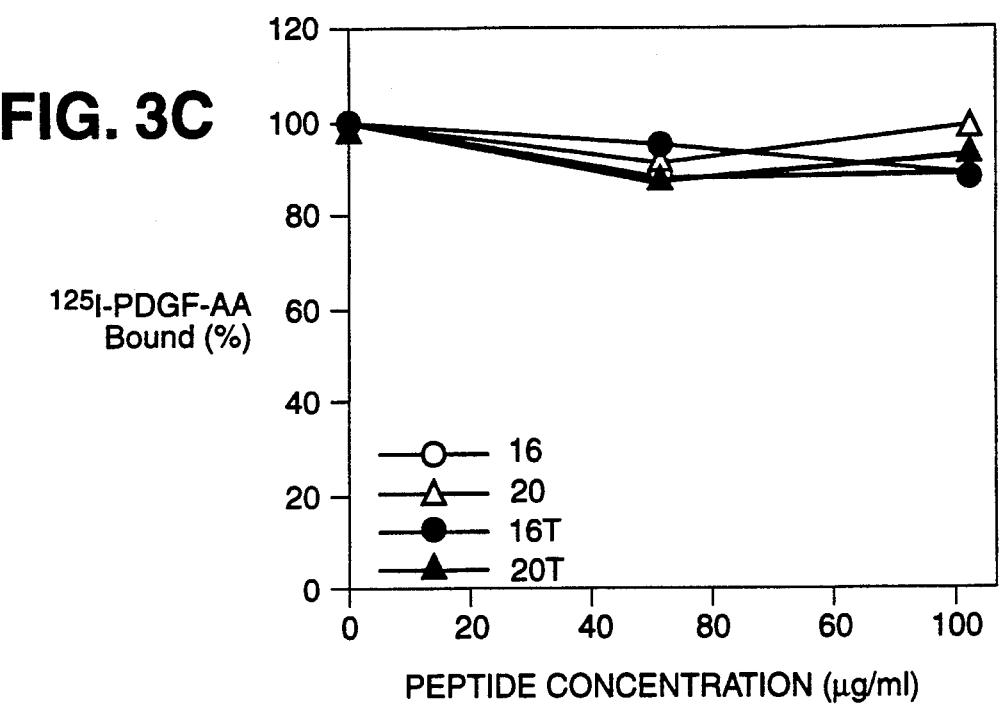

In comparative experiments, depicted in FIGS. 3A, 3B and 3C, peptides 16 and 16T were tested for antagonistic activity for both $^{125}$I-PDGF-AA and $^{125}$-PDGF-BB ($\alpha$ and $\beta$ receptors). The figures show that while peptide 16 had a marginal effect, 16T was an effective competitor for both PDGF-AA and PDGF-BB. Forty-four ug/ml (26 $\mu$m), and 57 ug/ml (33 $\mu$M) of peptide 16T gave 50% competition for receptor binding to $^{125}$I-PDGF-AA and $^{125}$I-PDGF-BB, respectively.

A control was carried out using peptides with randomized amino acid sequence—i.e., peptides 20 and 20T, the latter carrying the thioanisole modification on tryptophan. As shown in FIGS. 2A, 2B and 2C, the peptides did not compete for binding. The conclusion which must be reached from these experiments is that the amino acid sequence and a tryptophan modification are important for competitive behavior.

FIG. 3C shows that none of peptides 16, 16T, 20 and 20T compete for inhibition of $^{125}$I-EGF to EGF receptor. The peptide 16T thus is specific for PDGF receptor competition.

Example 4

The possible role of peptide 16T as an antagonist for PDGF activity in vivo was investigated. Following the methodology of Betsholtz et al., J. Cell Physiol 118: 203–210 (1984), the disclosure of which is incorporated by reference, [$^3$H] thymidine incorporation by human fibroblasts in the presence of various peptides was studied. Table IV shows these results infra. Table IV shows that PDGF-BB and EGF stimulated the incorporation of [$^3$H] thymidine into fibroblasts 4- and 5-fold, respectively. PDGF-AA gave lower stimulation, which is consistent with the results obtained by Nister et al., Cell 52: 791–799 (1988). The peptides 16 and 16T did inhibit PDGF-AA and PDGF-BB induced mitogenicity, but also EGF induced mitogenicity. This indicates that peptides 16 and 16T did not operate solely on the level of competition for receptor; rather, an additional mechanism is involved. Peptide 20, i.e., the control, showed a minor effect on ligand stimulated [$^3$H] thymidine incorporation, while peptide 20T showed some non specific inhibition activity. Peptide 16T was more efficient than peptide 16, and lowered background incorporation of [$^3$H] thymidine dramatically.

TABLE 4

Effect of the Peptides 16, 16T, 20 and 20T on ligand stimulated [$^3$H]thymidine incorporation in human foreskin fibroblasts. Figures represent mean of duplicates.

| Peptide | Control (cpm) | Ligand used for stimulation | | |
|---|---|---|---|---|
| | | PDGF-AA (cpm) | PDGF-BB (cpm) | EGF (cpm) |
| Control | 483 | 677 | 1918 | 2591 |
| Peptide 16 | 241 | 242 | 281 | 216 |
| Peptide 20 | 348 | 535 | 1541 | 2059 |
| Peptide 16T | 46 | 90 | 102 | 119 |
| Peptide 20T | 456 | 489 | 836 | 515 |

Example 5

Further experiments were carried out to study the effect of the peptides on intact cells; specifically, inhibition of ligand degradation was studied.

To do this, confluent human foreskin fibroblast cells in 12 well dishes were washed once with 1.0 ml of Ham's F-12 medium, supplemented with 1 mg/ml BSA. As described supra, those cells to be tested later for $^{125}$I-PDGF-BB degradation were preincubated with PDGF-AA to downregulate $\alpha$ receptors. Cells were then incubated with different concentrations of each of peptides 16, 16T, 20 and 20T together with $^{125}$I labelled PDGF-AA, PDGF-BB or EGF in 0.5 ml/well Ham's F-12 medium containing 1 mg/ml BSA. The mixtures were incubated for four hours at 37° C., the incubation medium was removed, and then precipitated with trichloroacetic acid at 10% final concentration. The amount of trichloroacetic acid non-precipitatable radioactivity in cell culture medium was taken as an estimate of ligand degradation—i.e., it represents ligand that had been internalized, degraded and released into the medium in the form of free $^{125}$I, $^{125}$I-Tyr, or low molecular weight fragments. This parameter was defined after four hours of incubation at 37° C.

Figure 4A:
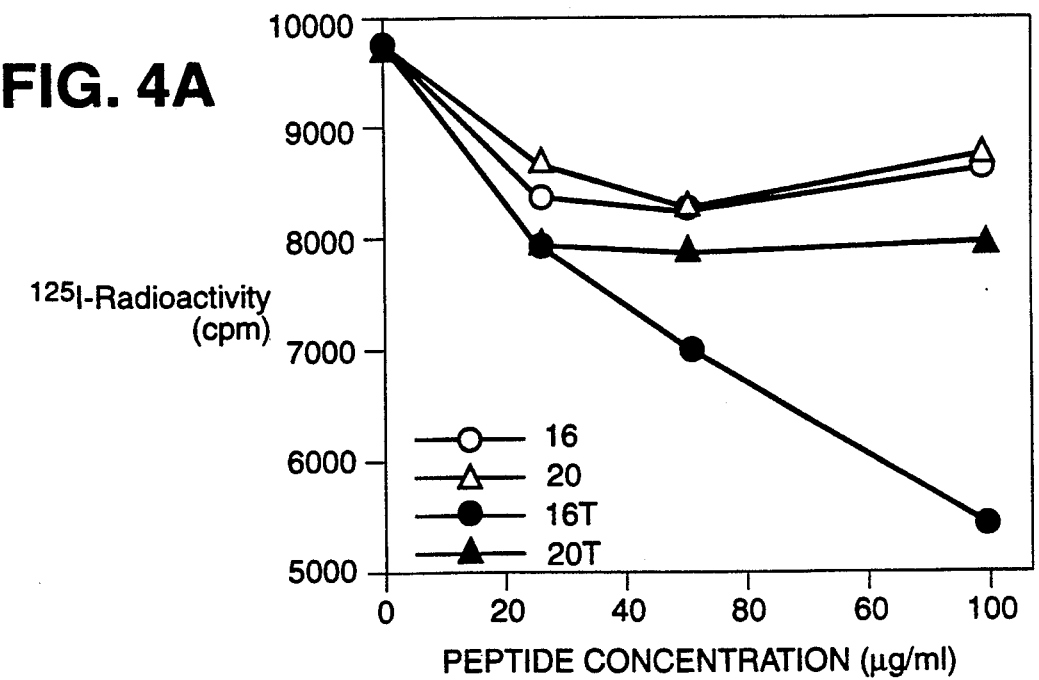
FIGS. 4A, 4B and 4C present data showing inhibiting effect of various PDGF derived peptides on $^{125}$I-labeled PGF-AA internalization and degradation.
Figure 4B:
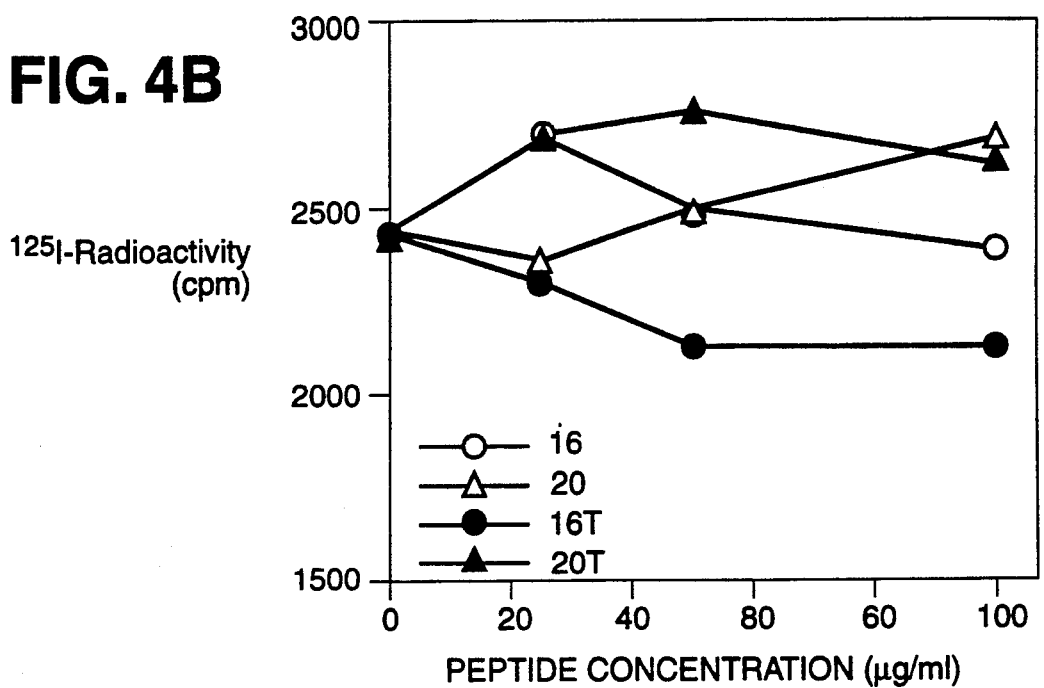
Figure 4C:
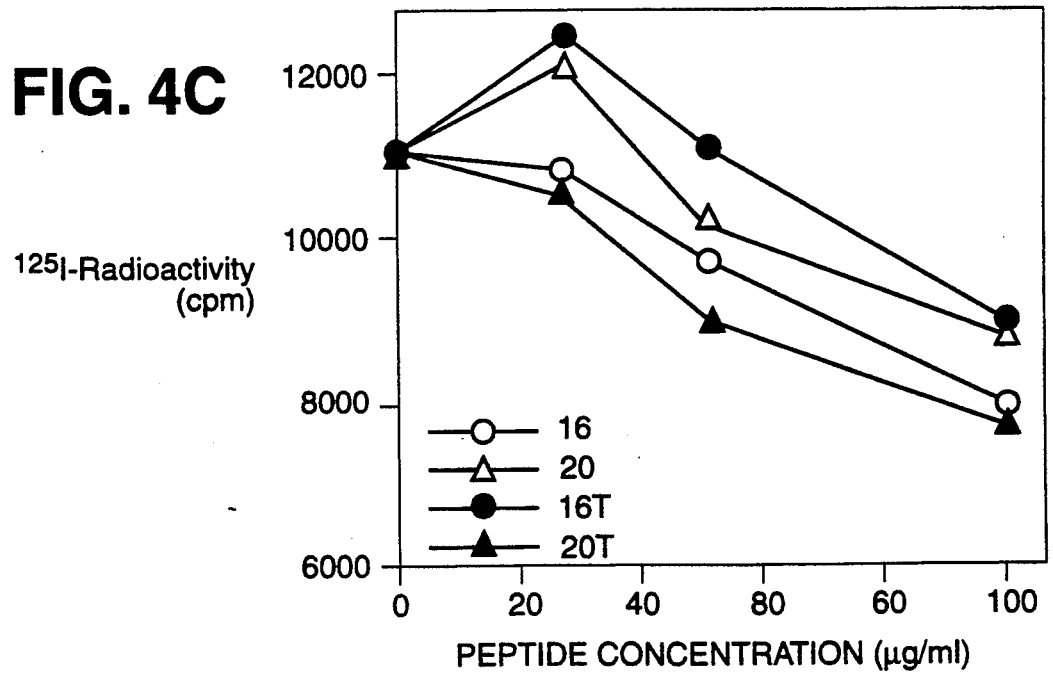

FIG. 4 shows that all peptides showed some inhibitory activity with respect to $^{125}$I-PDGF-AA degradation, with peptide 16T being most effective. The effect on PDGF-BB degradation was lower, with peptide 16T being the most potent. All peptides inhibited $^{125}$I-EGF degradation, but the peptides showed no difference with this parameter.

These results show that peptide 16T has an effect on cells which is a combination of specific inhibition at PDGF receptor level and an effect inside the cell which is not PDGF specific.

Example 6

The foregoing results show that peptide 16T interacts with both the $\alpha$ and $\beta$ receptors. As binding of PDGF to receptors leads to receptor internalization and downregulation, investigations were carried out to determine whether the interaction of PDGF and peptide 16T led to internalization and downregulation of receptors. To test this, confluent cells, as described supra, were washed once with binding buffer at 37° C., followed by incubation with different concentrations of synthetic peptide (0.5 ml BSA). Following this, the cells were incubated at 37° C. for four hours, followed by washing with 1 ml of ice cold buffer consisting of 20 mM Na-acetate, 150 mM NaCl, 0.2% BSA adjusted to pH 3.7 with acetic acid. The cells were then incubated for 10 minutes on ice in buffer, followed by two washings with 1 ml binding buffer, at pH 7.4. The number of PDGF receptors on the cell surface was estimated by incubation with $^{125}$I-PDGF-BB (~50,000 cpm) in 0.5 ml binding buffer for 60 minutes on ice, followed by washing, lysis and determination of cell bound radioactivity.

Results were negative—i.e., peptide 16T did not downregulate PDGF-$\alpha$ or $\beta$ receptor.

Example 7

Studies were carried out to determine if the interaction of peptide 16T with PDGF receptors was agonistic or antagonistic. This involved the study of dimerization and autophosphorylation of PDGF and EGF receptors in intact cells.

Confluent human foreskin fibroblast cells were used (25 cm$^2$ dishes of cultures). The cells were washed twice with binding buffer, as described supra, with 1 mg/ml BSA added thereto. This was followed by 90 minutes of incubation with one of synthetic peptides 16, 16T, 20 and 20T on ice. This was followed by addition of either PDGF-BB or EGF (300 ng/ml) and 60 minutes of further incubation. A dimerization assay was then carried out, basically following Eriksson et al., Growth Factors 6: 1-14 (1992). Essentially, receptors were cross linked for 20 minutes at room temperature in 1 mM BS³ (Bis(-sulfosuccinimidyl)suberate) in lysis buffer (0.5% Triton X-100, 0.5% deoxycholate, 30 mM Hepes, pH 7.4, 150 mM NaCl, 10 mM EDTA, 1 mM PMSF (phenylmethylsulfonyl fluoride), 1% Trasylol (aprotinin), 100 μM ortovandat, a phosphatase inhibitor). Cross linking was quenched by adding 70 mM methylammonium chloride for 10 minutes. Samples were then subjected to SDS gel electrophoresis in 4% slab gels, followed by electroblotting on to nitrocellulose membranes. The blocked membranes were incubated for two hours with affinity purified phosphotyrosine antibodies (Ek et al., J. Biol. Chem. 259: 1145-11152 (1984)), followed by three washes. Blots were then incubated for 45 minutes with peroxidase conjugated, affinity purified swine antirabbit IgG immunoglobulin. After an additional three washes, complexes were visualized using the ECL developing system.

Figure 5:
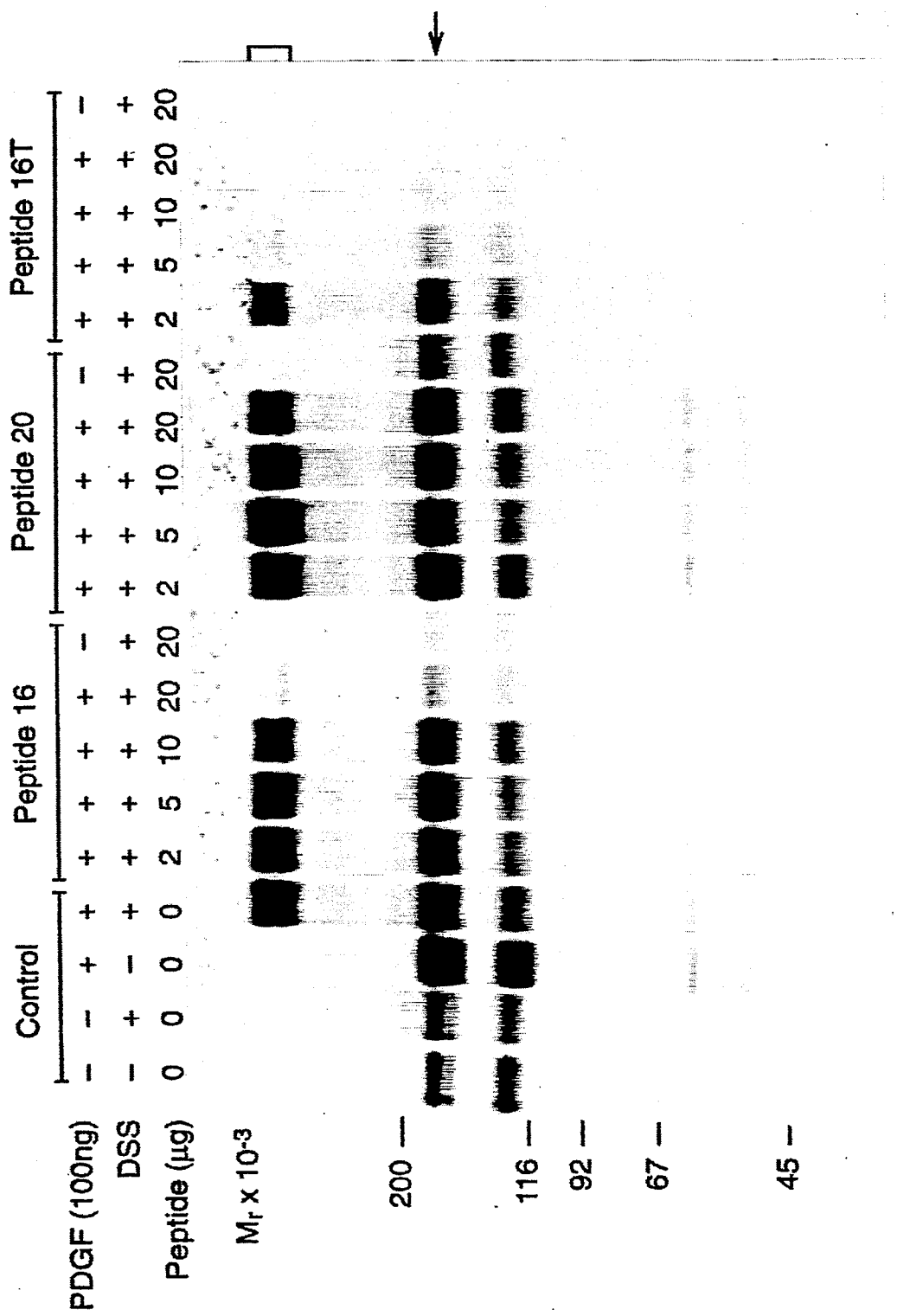
FIG. 5 shows the inhibition of receptor dimerization and autophosphorylation by peptide 16T.

The results, presented in FIG. 5, show that both PDGF and EGF induced autophosphorylation of receptors. After cross linking, most of the autophosphorylated receptors were visualized as fuzzy, double sized components (bracket of FIG. 5), probably representing dimers.

When peptide 16T was used, PDGF induced autophosphorylation and dimerization was inhibited by about 55%. There was no effect on EGF induced activity. Control peptide 20T showed no effect whatsoever. These results show that peptide 16T is an antagonist, rather than an agonist.

Example 8

Further experiments were carried out involving autophosphorylation and dimerization. These were more quantitative, as they used partially purified PDFG-β receptors.

A preparation of PDGF-β receptor, from Triton X-100 solubilized porcine uterus membranes and purified up to the Mono-Q chromatography step of Rönnstrand et al., J. Biol. Chem. 262: 2929-2932 (1987), was made, and the autophosphorylation assay described was carried out.

Approximately 100 ng of the receptor was incubated for 5 minutes at 0° C. with peptide 16T or peptide 20, at different concentrations. PDGF-BB (100 ng) was added and incubated for another 15 minutes. Incubation mixtures had a total volume of 40 ul and contained, as final concentration, 0.1% Triton X-100, 5% glycerol, 0.5 mM EGTA, 0.5 mM dithiothreitol, 20 mM Hepes, pH 7.4, 180 mM NaCl, 3 mM $MnCl_2$, and 1 mg/ml BSA. Four ul of 150 μM [$^{32}$P]ATP (containing $5 \times 10^6$ cpm of radioactivity) was added, followed by an additional 10 minutes of incubation at 0° C. Incorporation of radioactivity was terminated by adding 5 μl of 15 mM unlabelled ATP and 5 μl of 40 mM phenylphosphate. Samples were cross linked by incubating with 0.5 mM DSS (12.5 mM, in dimethyl sulfoxide) for 30 minutes at room temperature. The cross linking reaction was blocked by adding 50 mM methylammonium chloride, 20 mM Hepes, pH 7.4.

In the absence of peptide, PDGF induced autophosphorylation of its 180 KDa receptor and a 130 KDa degradation product, as shown in FIG. 5. Following covalent cross linking, most autophosphorylated material was seen as a double band at about 350 KDa.

When peptide 16T was present, as concentrations increased, both dimerization and autophosphorylation decreased. Nearly complete inhibition was obtained at 5 μg of peptide. Control peptide 20 showed no effect at concentrations up to 20 μg. Peptide 16 had an intermediate effect, with complete inhibition at 20 μg. These results parallel those obtained in the studies of ligand binding inhibition, discussed supra.

Example 9

Prior work has shown that each PDGF strand contains eight cysteine residues, but free SH groups have not been found. (Claesson-Welsh et al., Proc. Natl. Acad. Sci. USA 86: 4917-4921 (1989)). It was suspected that PDGF most probably contains an even number of interchain disulfide bridges, most likely two interchain bridges, and three intrachain bridges in each subunit. It was thought that interchain disulfide bridges would be more susceptible to reduction than the interchain disulfide bonds. In order to attempt to identify interchain bonds, partial reduction methodologies were employed.

Aliquots of recombinant PDGF-AA long splice variant were incubated with different concentrations of dithiothreitol ("DTT") for two hours at room temperature. These samples were then alkylated and analyzed by SDS-gel electrophoresis, using non reducing conditions. Silver staining followed.

Figure 6:
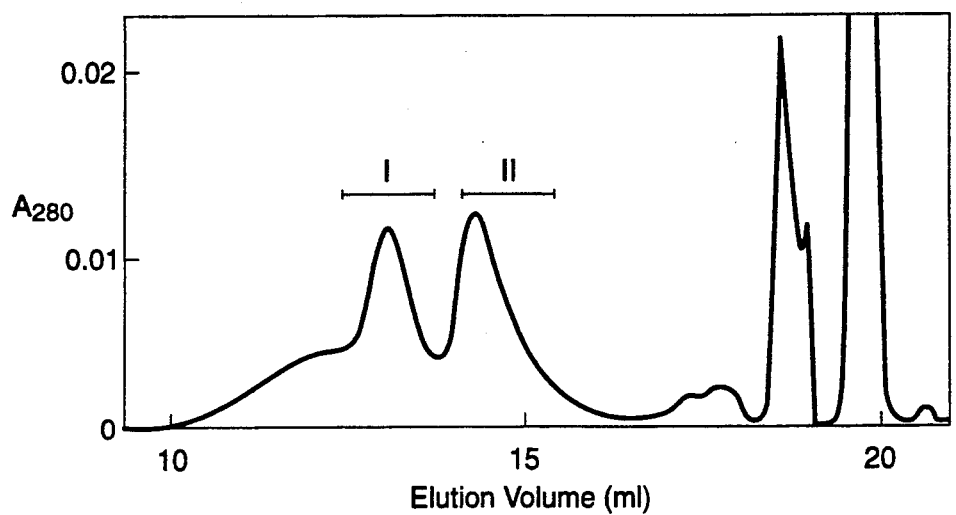
FIG. 6 shows elution of dimeric PDGF AA and monomeric PDGF A following reduction of dimeric form.
Figure 6A:
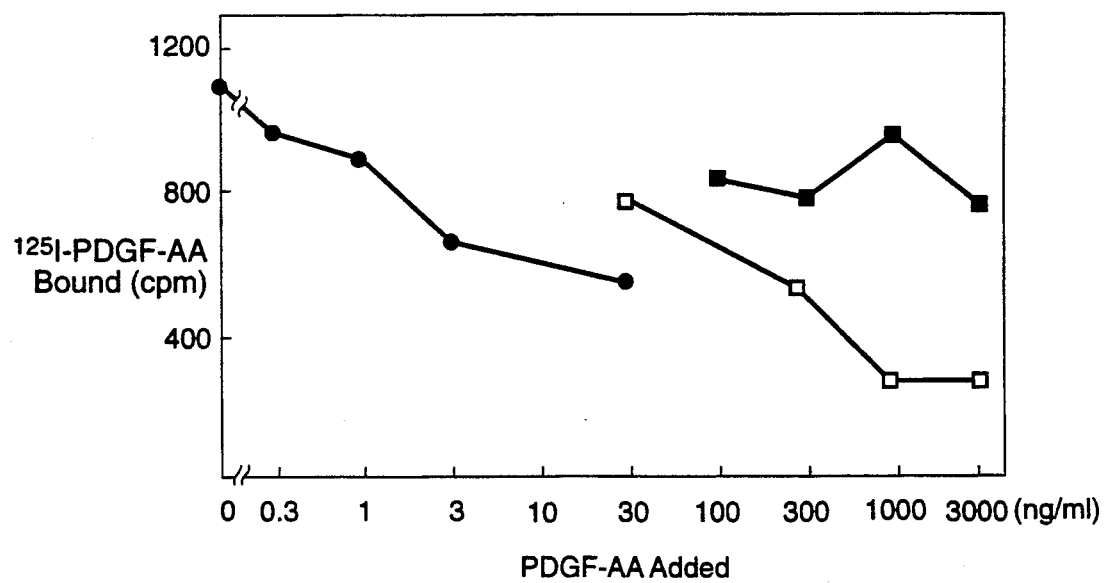
FIG. 6A shows competition for binding between PDGF-AA and $^{125}$I-PDGF AA.
Figure 6B:
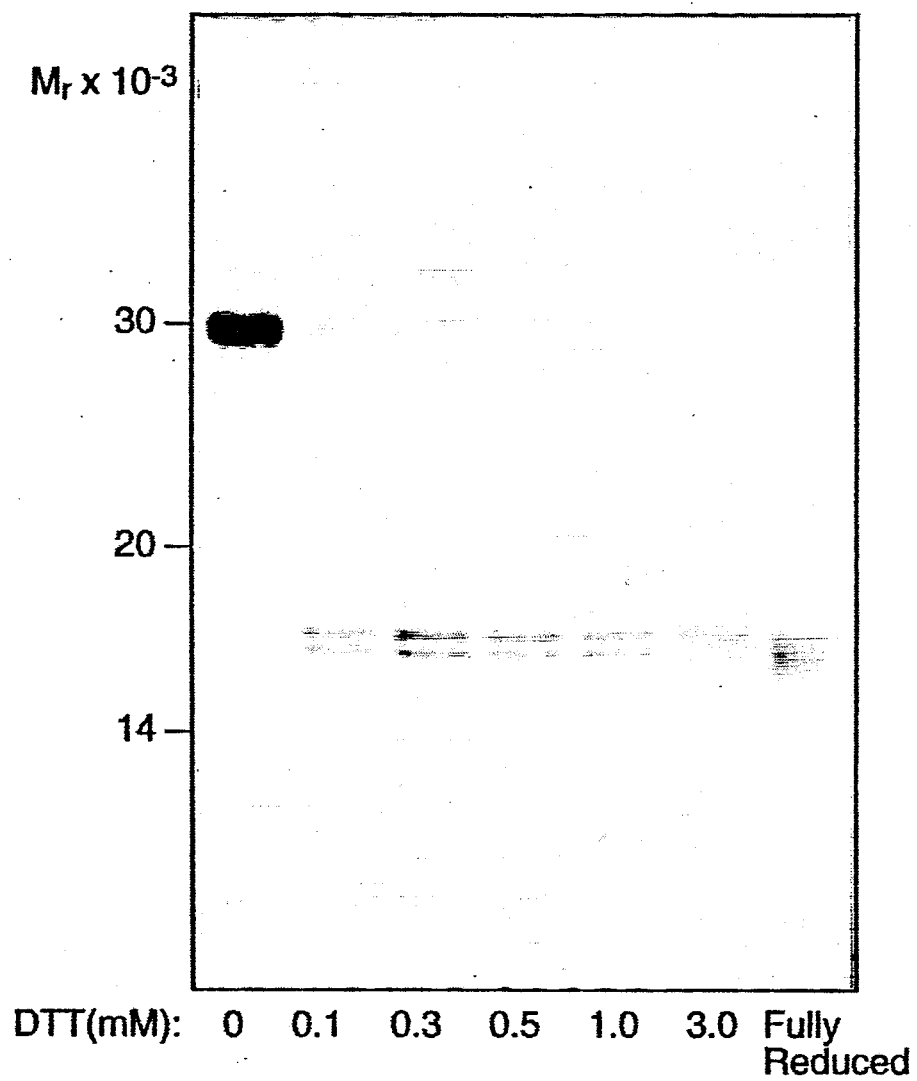
FIG. 6B shows the effect of the reducing agent dithiothreitol ("DTT") on dimeric PDGF-AA.

FIG. 6B shows that PDGF-AA gradually shifted from 30 KDa to 17 KDa—a shift from dimer to monomer—as the concentration of DTT increased. At 3 mM DTT, almost all PDGF appeared as a monomer, but the material migrated more slowly than fully reduced PDGF, suggesting the intrachain bonds remained.

The experiment confirms that interchain bonds are more susceptible to reduction than intrachain bonds, and suggests the use of this methodology to prepare sufficient material to identify the particular residues involved.

Example 10

The experiment of Example 9 was carried out on a preparative scale. 90 μg of recombinant, long splice PDGF-AA was treated with 3 mM DTT in 220 μl of 0.36M Tris.HCl pH 8.2 for two hours at 20° C. This exposed interchain SH bonds, which were then reacted with 9 mM iodoacetic acid in the same solution for 15 minutes to alkylate the groups. The alkylated monomers were isolated by gel chromatography on Superose 12 ($1 \times 30$ cm) in 6M urea, 0.3M NaCl and 1M acetic acid at a flow rate of 15 ml/h. Two peaks eluted, as shown in FIG. 6. The fractions were analyzed via SDS-gel electrophoresis following Blobel et al., J. Cell Biol. 67: 835-851 (1975), followed by silver staining. The gel work showed that the two HPLC fractions were monomers and dimers. Monomeric material was isolated by desalting via reversed phase HPLC using a narrow bore Brownlee Aquapore C1 column. The material was divided into two portions. One was used in receptor binding assays, the other was fully reduced. The experiments on these two fractions follow, those involving full reduction being presented first. Receptor binding was carried out using the protocols of Example 14, infra.

Example 11

The partially reduced, monomeric PDGF-A was fully reduced by 20 mM DTT in 4M guanidine-HCl, 1M Tris.HCl, pH 8.0 and 10 mM EDTA for two hours at 37° C. This fully reduces the monomers, which were then treated with 4-vinylpyridine (incubation for two hours, room temperature). The reduced monomers were desalted, as described supra and dried. The treatment with 4-vinylpyridine pyridylethylates cysteine residues, rendering them visible at 254 nm.

Reduced material was digested with Glu-C protease at an enzyme/substrate ration of 1/50 (w/w) for 15 hours at 37° C. in 200 ul of 2M urea and 0.1M ammonium bicarbonate. At the end of the reaction time, the mixture was applied to a Brownlee Aquapore C4 (2.1×30 mm) narrow bore column, and fragments were eluted by a linear gradient of -n-propanol (0–27% over 60 minutes), 0.16% trifluoroacetic acid at a flow rate of 100 ul/min. Effluent was monitored using a photodiode array detector, and spectral data were collected between 200 and 300 nm.

Figure 7A:
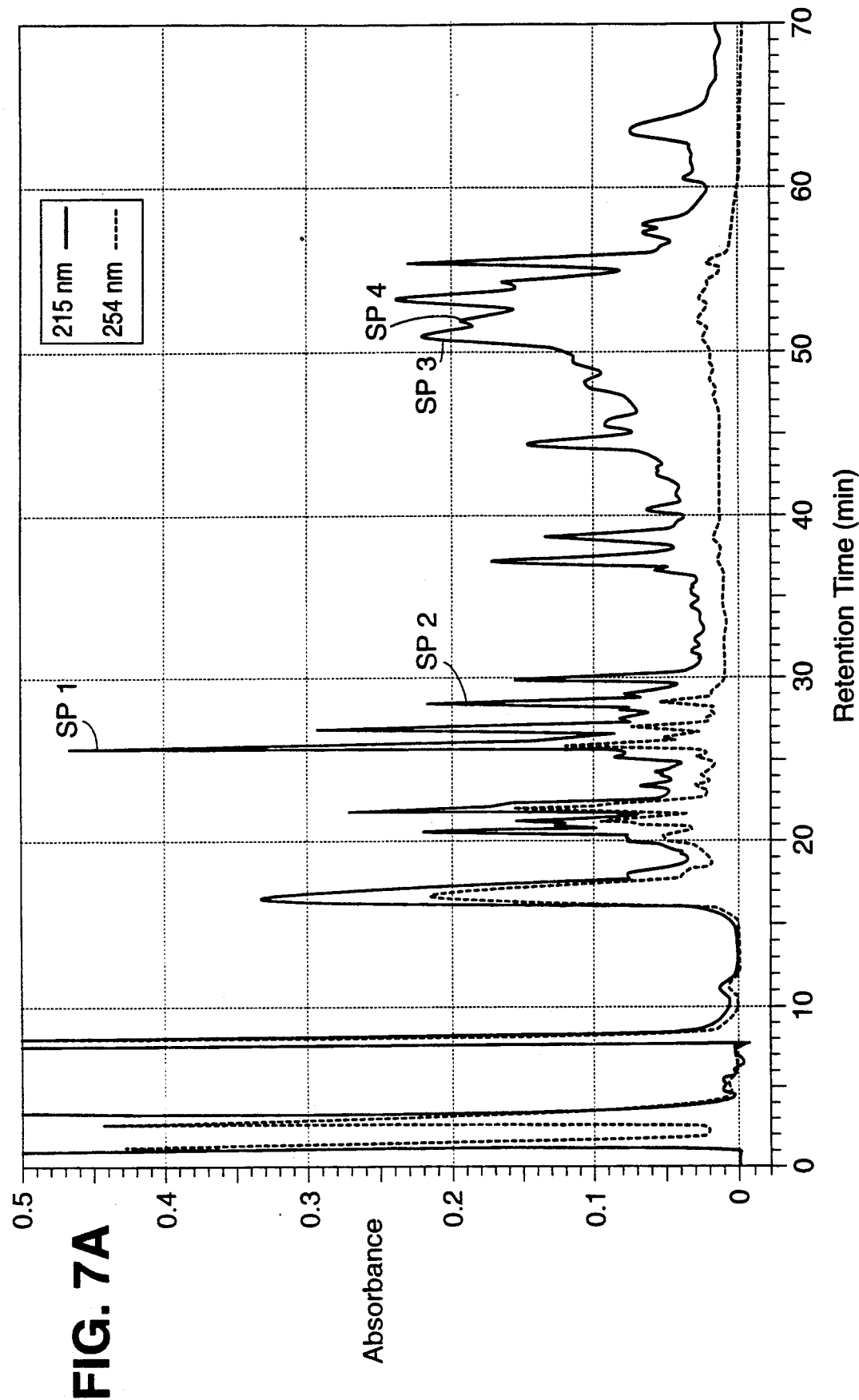
FIG. 7A shows HPLC information secured from proteolytically degraded, partially reduced monomeric PDGF-A.

These HPLC fractions were dried onto polybrene treated glass fiber discs and subjected to well known Edman degradation. HPLC information is presented in FIG. 7A. The sequences which were found to contain cysteine residues are shown in FIG. 7B (i.e., sequences SP1, 2, 3 and 4). In FIG. 7B, the "#" is a carboxymethyl cysteine, and "@" is a pyridylethyl cysteine.

Those cysteine residues involved in interchain disulfide bonds should appear as carboxymethyl cysteine, due to the action of iodoacetic acid, while intrachain bond forming cysteine should appear as pyridylethylcysteine. These results show that the 2nd and 4th cysteine residues in the PDGF-A monomer, form the interchain, disulfide bounds.

Example 12

In order to pursue the results of Example 11 further, a cDNA sequences coding for PDGF molecules were mutated so that Cys 123 and Cys 132 were serine. To do this, cDNA for the short splice version of PDGF-A (Betsholtz et al., Nature 320: 695–699 (1986)) was used. Following Kunkel et al., Meth. Enzymol 154: 367–382 (1987), codons corresponding to one or both of the residues, resulting in pSV Ser 2, pSV Ser 4, and pSV monoA were produced. A uracil containing template coding wild type PDGF-A was also produced. Similarly, corresponding codons in the B chain cDNA (Cys 124, Cys 133 of the PDGF B stop variant) were mutated to yield pSV monoB, together with conversion of codon 191 to a stop codon, thereby yielding a soluble product (Östman et al., Cell Reg. 2: 503–512).

Figure 12:
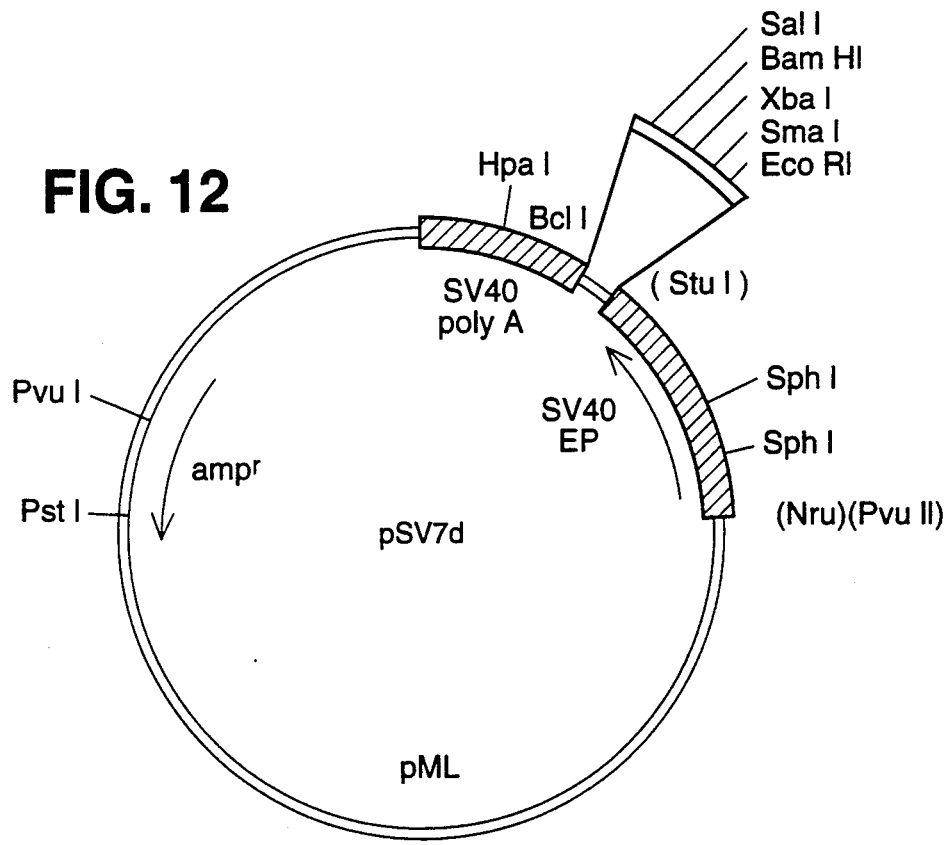
FIG. 12, labelled PRIOR ART, is the restriction map of plasmid pSV7d.

To produce the vectors pSV monoA, pSVA Ser 2 and pSV Ser 4, mutated fragments were cloned into the EcoRI/Bal 1 sites of vector pSV-PDGF-A 102A (pSVA), as taught by Östman et al., J. Bio. Chem. 263: 16202–16208 (1988), in which wild type fragments were excised. The construct pSV monoB was generated by cloning into the EcoRI site of plasmid pSV7d. This plasmid is well known and its structure is given in Truett et al., DNA 4(8): 333–349 (1985), FIG. 2. It is also presented as FIG. 12.

Example 13

The constructs of Example 12, including pSVA and pSVB stop were transfected into COS cells following Östman et al., Cell Reg. 2: 503–512 (1991), using 20 ug of plasmid DNA and $0.5 - 1 \times 10^6$ cells in 60 mm culture dishes. Two days after transfection, metabolic labeling was performed. This was accomplished by growing cells overnight in 1.5 ml of cysteine free MCDB 104 medium, supplemented with 0.1 mCi [$^{35}$] cysteine/ml, 10% dialyzed fetal calf serum, and antibiotics. After labelling, media were collected and cleared of cell debris via centrifugation. Cells were washed once in PBS, collected by scraping, and lysed in 0.5 ml of 0.5M NaCl;, 20 mM Tris.HCl, pH 7.5, 0.5% Triton X-100%, 1% aprotinin, and 1 mM PMSF. Cell lysates were centrifuged for 15 minutes at 10,000 g, and supernatants subjected to immunoprecipitation using antiserum to PDGF-AA. Essentially, the samples were precleared by incubation with 15 ul of normal rabbit serum at 4° C. for 1 hour, followed by addition of 60 ul of a 50% Protein-A-Sepharose slurry in PBS. This was incubated at 4° C. for 30 minutes, and beads were removed by centrifugation. Following this, 15 ul of anti PDGF AA or anti-PDGF BB were added, followed by two hours of incubation at 4° C. This was again followed by incubation with Protein A Sepharose (supra). The beads were then washed five times with 0.5M NaCl, 20 mM Tris, pH 7.5, 5 mg/ml BSA, 1% Triton X-100 and 0.1% SDS, as well as once with 20 mM Tris-HCl, pH 7.5. Immunocomplexes were eluted by adding 200 ul of nonreducing sample buffer, with three minutes of incubation at 95° C. Half of the eluted material was reduced by adding DTT (final concentration, 10 mM), and two minutes of incubation at 95° C. Alkylation was carried out with 50 mM final concentration iodoacetamide. Samples were analyzed by SDS gel electrophoresis, using 12–18% polyacrylamide gels and fluorography.

Figure 8A:
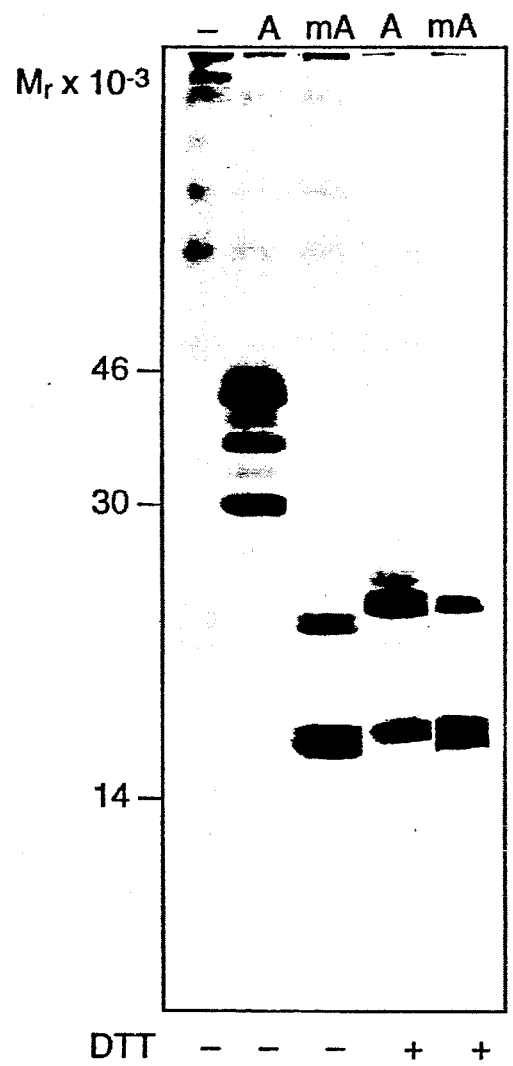
FIGS. 8A and 8B show analysis of immunoprecipitated, conditioned medium following labelling with [$^{35}$S]-cysteine.
Figure 8B:
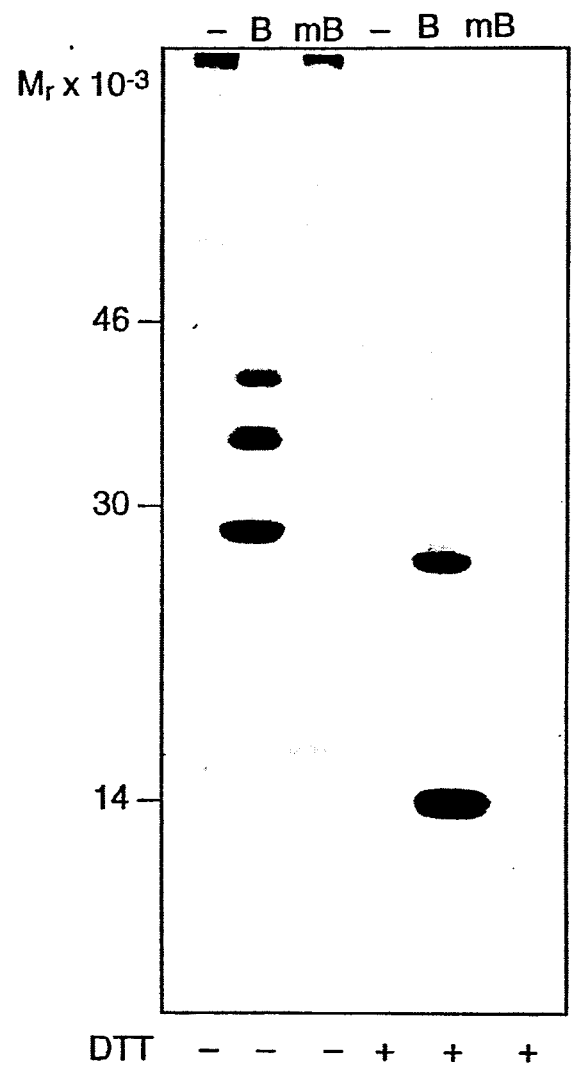

Results are shown in FIGS. 8A and 8B. FIG. 8A shows that when conditioned medium from [$^{35}$S]-cysteine labelled cells was immuno-precipitated, only monomeric forms were found. When analyzed under reducing conditions, the PDGF mono A shifted in the gel, indicating that intrachain disulfide bonds were present. Also, anti-wild type PDGF-AA antiserum recognized the mono-A, supporting the theory that the conformation of PDGF mono A is similar to the two chains in the dimer.

The parallel mutant, PDGF mono B showed the same pattern of analysis, as will be seen in FIG. 8B.

Example 14

The following experiments describe receptor binding assays using the recombinant proteins produced following Example 13.

Figure 9:
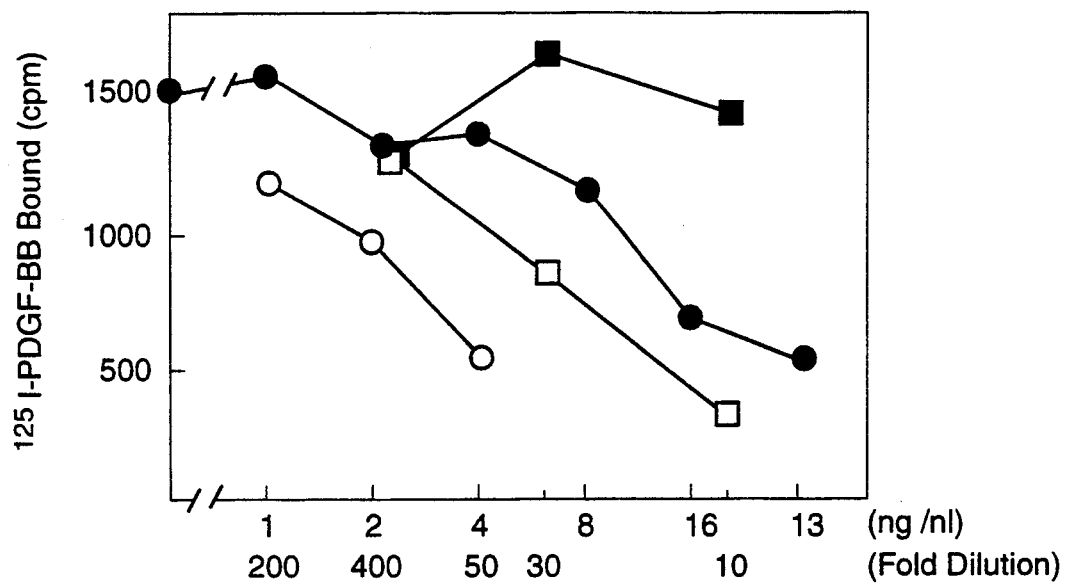
FIG. 9 shows experiments involving cell growth and competition between $^{125}$-PDGF-BB and serial dilutions of peptides.

In the case of recombinant proteins, thirty six hours after transfection, culture medium was changed to 1.5 ml of serum free medium, and culture continued for 48 hours. Media were then applied onto a narrow bore, reversed phase C4 HPLC column (2.1×30 mm) for desalting and concentration. The column was washed with 0.1% trifluoroacetic acid, and retained material eluted with 70% acetonitrile in 0.1% trifluoroacetic acid. After evaporation, samples were dissolved in one tenth of the original volume of PBs, and binding to PDGF-α and β receptors was studied. The study was carried out by analyzing serial dilutions and their ability to compete with $^{125}$I-PDGF-AA and $^{125}$I-PDGF-BB for binding to AG-1518 cells. Cells had been grown in Falcon 24-well plates to confluence, followed by one washing in binding buffer (PBS with 1 mg/ml BSA, 0.9 mM CaCl$_2$, 0.5 mM MgCl$_2$). Cultures were incubated at 0° C. for two hours in 200 ul of binding buffer containing the different dilutions as shown in FIG. 9, or known amounts of PDGF-AA or PDGF-BB for standardization. Cells were washed twice with binding buffer, after which radiolabelled PDGF-AA or PDGF-BB (0.5-2 ng; 15,000-30,000 cpm) in 200 ul binding buffer was added. This was incubated at 0° C. for one hour, after which cells were washed five times with binding buffer, followed by lysis in 200 ul of 20 mM Tris.HCl, pH 7.5, 1% Triton X-100 and 10% glycerol, at room temperature for 20 minutes. Solubilized $^{125}$I radioactivity was measured in a geiger counter.

Where β-receptor assays were carried out, prior depletion as discussed supra, was also used.

The results, as presented in FIG. 9, show monoB competed relatively well. Data are not shown for PDGF monoA, which did not detectably bind to α receptor.

Example 15

It was important to determine whether the binding of monomeric PDGF to PDGF receptors induced agonistic or antagonistic effects. The PDGF-mono B molecule was therefore tested for its ability to activate β-receptor in an autophosphorylation assay. Conditioned media from cultures of COS cells transfected with pSV B stop, pSV monoB or from mock transfected cells were desalted and concentrated as described supra. A radioreceptor assay was carried out to determine receptor binding activity, using standard techniques. Once this was accomplished, media from pSV monoB or pSV monoB stop transfected cells were adjusted with mock transfected medium to receptor binding activity of 100 ng/ml. PAE cells expressing PDGF B receptors (Westermark et al., Proc Natl. Acad. Sci. USA 87: 128–132 (1990), grown in 25 cm$^2$ dishes were labeled in serum and methionine free MCDB 104 medium supplemented with 0.1 mg/ml BSA and 0.1 ml [$^{35}$S] methionine/ml for three hours at 37° C. Cells were stimulated with 1 ml of different concentrations of conditioned media for 30 minutes at 4° C. A positive control was set up using 1 ml of mock transfected medium with 100 ng/ml of recombinant PDGF-BB. Cells were washed once with PBS, scraped into a lysis buffer of 20 mM Tris.HCl, pH 7.5, 150 mM NaCl, 10 mM EDTA, 0.5% deoxycholate, 0.5% Triton X-100, 30 mM pyrophosphate, 1% aprotinin and 1 mM PMSF, followed by centrifugation for 15 minutes at 10,000 g for clearance. Half of this lysate was incubated at 40° C. for two hours with 5 ul of antiserum against a peptide derived from the PDGF-β receptor (Claesson-Welsh et al., J. Biol. Chem. 264: 1742–1747 (1989)); the other half with 1 ul of antiserum against phosphotyrosine (Ek et al., J. Biol. Chem. 259: 1145–11152 (1984)). Immunocomplexes were precipitated with 60 ul of a 50% slurry of Protein-A-Sepharose in PBS, after which beads were washed three times with lysis buffer, twice with 20 mM Tris.HCl, pH 7.5, 0.5M NaCl, 1% Triton X-100, and once in distilled water. Elution of immunocomplexes was performed by adding 100 ul of sample buffer containing 4% SDS, 0.2 mM Tris.HCl, pH 8.8, 0.5M sucrose, 5 mM EDTA, 0.01% bromophenol blue and 2%-mercaptoethanol. Immunocomplexes were analyzed by SDS-gel electrophoresis, using a 7% acrylamide gel and fluorography.

FIGS. 10A and 10B show these results. In FIG. 10A, analysis of immunoprecipitates using SDS-gel electrophoresis shows that both pSVB stop and pSV monoB stimulated autophosphorylation. In order to determine whether PDGF-mono B caused dimerization of the receptor, the β receptor expressing PAE cells were labeled with [$^{35}$S] methionine and stimulated with concentrated conditioned media from COS cells transfected with either of the relevant constructs. In these experiments, the labeled PAE cells were incubated for 90 minutes at 4° C., with 1 ml portions of concentrated conditioned media from COS cells transfected with pSVB stop, pSV monoB or the mock transfectants. Cells were washed once with PBS and lysed in solubilization buffer containing 20 mM Hepes, pH 7.4, 100 mM NaCl, 0.5% Nonidet P40, 10% glycerol, 1 mM PMSF and 1% aprotinin for 20 minutes at 4° C., followed by centrifugal clearance (10,000 g, 30 minutes). Crosslinking was performed with 1 mM BS$^3$ for 30 minutes at room temperature. Reaction was halted by incubation in 50 mM Tris.HCl, pH 7.5, for 10 minutes at room temperature. Immunoprecipitation and analysis was as above. Both PDGF mono B and PDGF-BB caused dimerization, as can be seen in FIG. 10B.

Example 16

Experiments were carried out to determine the arrangement of the interchain disulfide bonds between the second and fourth cysteines. To do this two new mutants were constructed, i.e., PDGF A Ser 2 with the second residue mutated to a serine residue and PDGF A Ser 4 with the fourth residue mutated to a serine residue. COS cells were transfected with pSVA(A), pSVA Ser 2, pSVA Ser 4, or both of pSVA Ser 2 and pSVA Ser 4. If interchain binding occurs between corresponding cysteine residues (e.g., 2nd cysteine to 2nd cysteine, or 4th cysteine to 4th cysteine), then cells transfected with pSVA Ser 2 or pSVA Ser 4 alone will not form dimers. Indeed, dimerization should only occur in a co-transfectant.

Cells were labelled with [$^{35}$S] cysteine, conditioned medium or medium from mock-transfected COS cells was immunoprecipitated using anti-PDGF AA antiserum, and precipitates were analyzed via SDS-gel electrophoresis, with or without DTT, followed by fluorography.

Figure 11A:
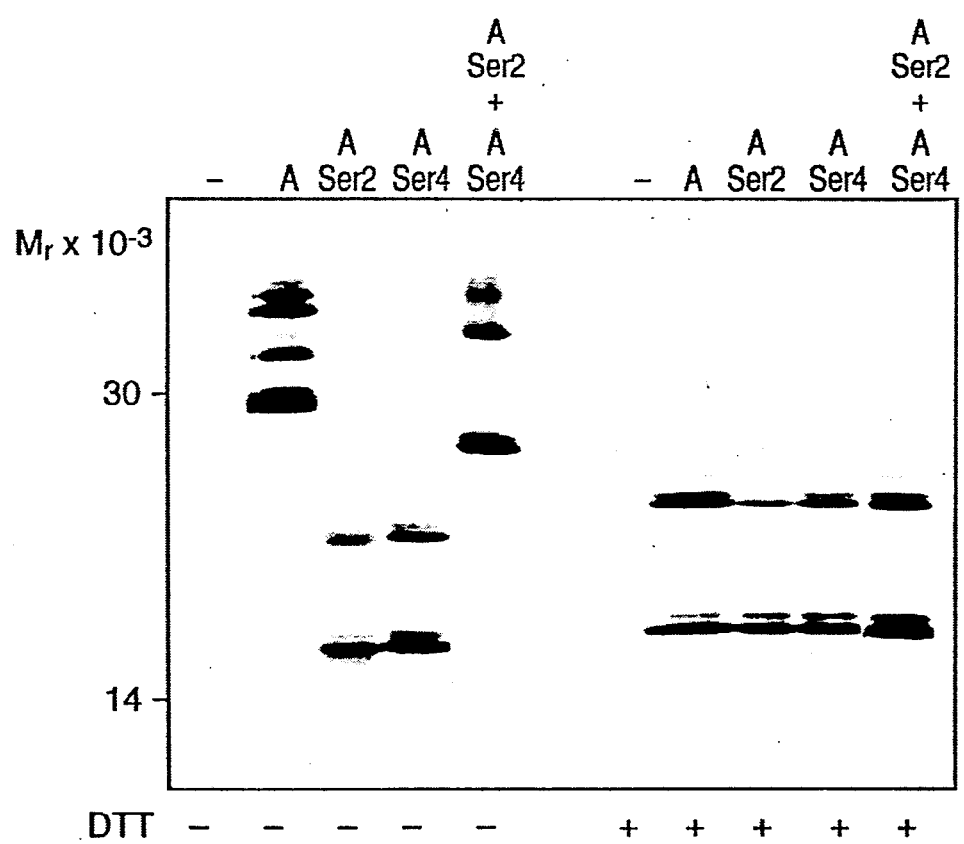
FIG. 11A shows studies on PDGF-AA dimer formation.

FIG. 11A shows that dimers were only found in the absence of DTT in the cotransfectants, showing that cross linkage was occurring. From this it can be concluded that the 2nd and 4th cysteine residues are disulphide bonded in crosswise fashion in the PDGF dimer.

Example 17

Figure 11B:
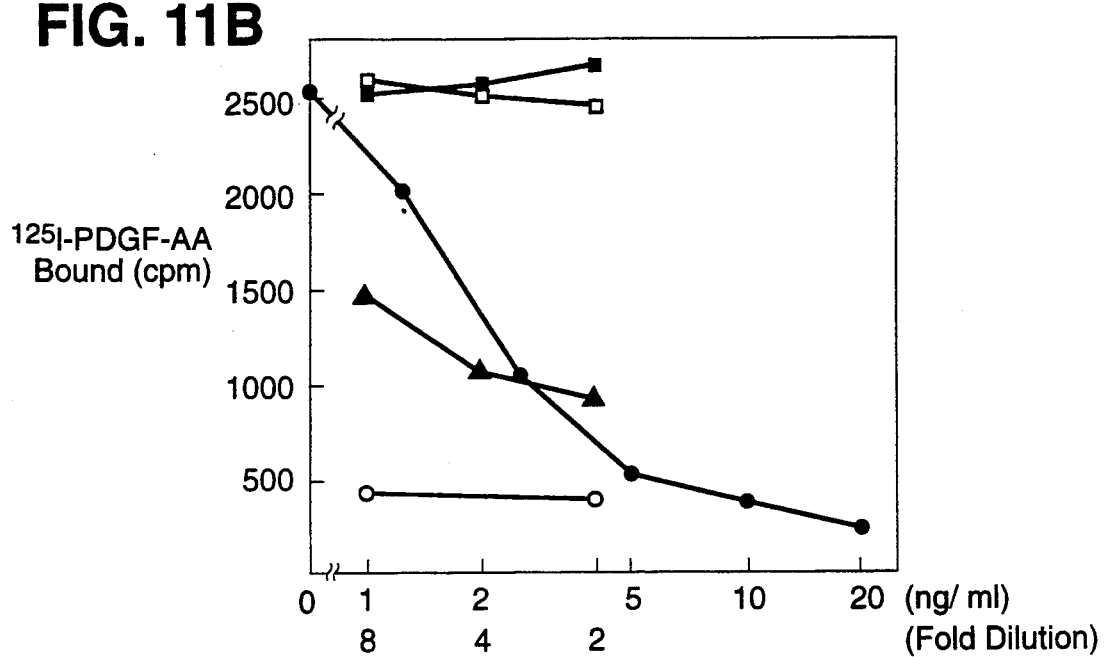
FIG. 11B shows antagonistic activity of single bonded dimers

Tests were carried out to determine the activities of the transfectants described supra. Conditioned medium from the pSVA, pSVA Ser 2, pSVA Ser 4, and pSVA Ser 2 and pSVA Ser 4 transfectants were concentrated, desalted, and then combined with $^{125}$I-PDGF-AA to test for binding to the α receptor. FIG. 11B shows that there was competition only in the presence of the co-transfectant.

The experiments presented supra show that various peptides and modified peptides derived from PDGF chains act as antagonists and agonists to the PDGF molecule. Preferred antagonistic peptides contain epitopes from two regions of the PDGF-B chain. The resulting peptides have amino acid sequences which, however, are not found in either wild type PDGF monomer. A preferred family of such peptides can be represented by the formula Ala Asn Phe Leu Val X(Y)n Glu Ile Val Arg Lys Lys Pro (SEQ ID NOS: 1, 2, 3, 4) where X is tryptophan or modified tryptophan, Y is any amino acid, and n is a whole number of 0 to 35. Especially preferred antagonists are the peptides referred to herein as "16" and "16T", having the amino acid sequence:

Ala Asn Phe Leu Val Trp Glu Ile Val Arg Lys Lys
Pro (SEQ ID NO: 3)

and

Ala Asn Phe Leu Val Xaa Glu Ile Val Arg Lys Lys Pro
(SEQ ID NO: 4)

respectively, where "Xaa" stands for thioanisolated tryptophan. Peptide 16T is far more efficient in competing with PDGF for receptor binding. The variant 16 NPS, in which tryptophan is coupled to 2-nitrophenylsulfenyl, is also more active as an antagonist than peptide 16. There is no immediate explanation for why these derivatives are superior to the original peptide 16, which is also active. The 13 amino acid sequence presented supra appears to be key to inhibitory/antagonistic activity. Further deletion of C-terminal amino acids, as indicated supra, resulted in insolubilization of the peptide, and thus an inability to study it. Truncation at the N-terminal end led to loss in activity.

Previous studies have shown that amino acids 105–144 of the B chain of PDGF are important to interaction with the B receptor (LaRochelle et al., Science 248: 1541–1544 (1990)). Additional studies have led to identification of Asn-115, Arg-154 and Ile-158 as important in binding (Östman et al., J. Biol. Chem. 266: 10073–10077 (1991)). The particularly preferred peptide 16 contains amino acids 116–121 and 157–163 of PDGF-B, and thus contains some amino acids close to those identified by Östman et al. as being important; however, it must be noted that the derivatives of the invention inhibit binding to both the α and β receptors, a property not recognized by the prior work in this field. Also, the evidence presented herein shows that even minor modifications in peptide structure have profound effect on antagonistic activity. The antagonistic effect of such peptides suggests their use in conditions characterized by excess or undesirable PDGF activity. These conditions include those discussed in the "Background" section, supra, as well as chronic inflammatory conditions.

In a manner somewhat similar to that involved in identifying PDGF antagonists, analysis of the pattern of SH binding in PDGF dimers led to identification of PDGF derivatives with agonistic activity. Specifically, when the second and fourth cysteine residues of PDGF-B were mutated to serine, the resulting derivative was agonistic to PDGF. Cysteine is unique in its ability to form disulfide bonds with other cysteine residues; thus, it can be assumed that modification of the second and fourth cysteine residue in the PDGF-B monomers will lead to generation of agonists. Such modification may include substitution of either or both cysteine residues with another amino acid, deletion of either or both, alteration, either chemically with, e.g., a blocking group or other means, as well as any other means which prevents interchain bonding. The only requirement is that both the second and fourth cysteine residues be modified in the same monomer.

In connection with the observation on PDGF-B, it must be noted that other molecules, including vascular endothelial growth factor (vascular permeability factor or VEGF; see Keck et al., Science 246: 1309–1312 (1989); Leung et al., Science 246: 1306–1309 (1989)), and placental growth factor (Maglione et al., PNAS 88: 9267–9271 (1991)), show cysteine structures paralleling that of PDGF-B. The observations made herein suggest correlation to these other molecules, given the structural similarities.

While PDGF-A monomers were not nearly as active as the modified PDGF-B monomers, partially reduced, alkylated PDGF-A monomers did show some activity.

Identification of the cross-molecular bonds as being involved in the formation of PDGF dimers has several very important ramifications. The first of these is the ability to control the production of a heterodimer PDGF-AB. Under normal circumstances, the binding of monomer A to monomer B is not favored over the formation of homodimers. The recognition of the cross bond, however, enables one to produce PDGF AB exclusively, subject to the single restriction that the dimer only contains a single intermolecular bond. Co-transfection of a cell with a nucleic acid molecules coding for one monomer lacking cysteine at one of the second or fourth wild type positions, and a second molecular lacking the cysteine at the other listed wild type cysteine position guarantees high production of PDGF AB. For example, if the first sequence codes for PDGF A without cysteine at the second position, and PDGF B without cysteine at fourth position, a dimer of PDGF AB will still form, because the fourth cysteine of PDGF A can still bind the second position of PDGF B. On the other hand, dimeric PDGF AA will not form, because although the requisite fourth cysteine is present, the second cysteine is eliminated. Similar considerations dictate the absence, of PDGF BB from such a system. One may, of course, produce homodimers by cotransfection with nucleic acid sequences lacking the second cysteine and the fourth cysteine, but otherwise not modified. One may also transfect two separate cell samples, each with a different nucleic acid sequence, so that dimerization may occur, e.g., in the culture medium. Thus, one aspect of the invention is a kit for production of the dimers described supra, with separate nucleic acid portions, each of which codes for the desired monomer.

The invention thus encompasses dimers produced in accordance with the principles herein, i.e., having only a single intermolecular disulfide bond. The amino acid positions described for the cysteine residues merely need modification, either by substitution by another amino acid, deletion, blocking, and so forth. It has been shown that such a PDGF AA molecule competes for binding. Antagonists could be designed from these molecules in which one of the chains is further modified to prevent binding to the receptor. These antagonists could then be directed to form a specific heterodimer with a wild type chain by virtue of modifying cysteine 2 or cysteine 4 in either molecule. Such molecules would act as antagonists as they would bind to receptor but inhibit receptor dimerization, which is necessary for activity, from taking place.

Disulfide bonding between two protein monomers to form a dimerized molecule is not uncommon. The invention also encompasses the production of "hybrid" dimers where one chain is either PDGF A or PDGF B, and this is bound, via a single disulfide bond, to another protein, such as a growth factor or, e.g., VEGF.

The peptide antagonists of the invention are preferably those which have amino acid sequences which are not found in either of wild type PDGF A or PDGF B. Especially preferred are those which have an amino acid sequence corresponding to amino acids 116–121 and 157–163 of PDGF B.

The invention as described herein thus embraces modifiers of PDGF activity, including agonists and antagonists. These, administered to a subject in need of modified PDGF activity in effective amounts, i.e., amounts sufficient to normalize PDGF activity in the subject to which they ar administered. Conditions such as atherosclerosis and fibrotic diseases can be treated in this manner. The mode of administration and dosage will vary depending upon the particular individual and the condition being treated. Mode of administration and dosage and the choices thereof are easily determined by the skilled artisan, and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated platelet derived growth factor agonist which binds to PDGF-β receptor and comprises amino acids 97-180 of PDGF-B monomer with the proviso that residues 124 and 133 are not cysteine.

2. The agonist of claim 1, wherein at least one of residues 124 and 133 is serine.

3. The agonist of claim 1, wherein both of residues 124 and 133 are serine.

4. Isolated nucleic acid molecule coding for the agonist of claim 1.

5. Plasmid containing the isolated nucleic acid molecule of claim 4.

6. Cell line transfected with the nucleic acid molecule of claim 4.

7. Cell line transfected with the plasmid of claim 5.

8. Method for causing receptor dimerization and autophosphorylation in a cell having PDGF-β receptors on its surface comprising administering to a cultured cell having PDGF-β receptor on its surface an amount of the agonist of claim sufficient to cause receptor dimerization and autophosphorylation in said cell.

* * * * *

UNITED STATES PATENT AND TRADEMARK OFFICE
CERTIFICATE OF CORRECTION

PATENT NO. : 5,326,695
DATED : July 5, 1994
INVENTOR(S) : Maria Andersson et al

It is certified that error appears in the above-indentified patent and that said Letters Patent is hereby corrected as shown below:

| Column | Line | | |
|--------|------|---|---|
| 1 | 56 | "The receptor" should read | --The $\alpha$ receptor-- |
| 2 | 12 | "Modified One" should read | --modified. One-- |

Signed and Sealed this

Twenty-seventh Day of December, 1994

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i x ) FEATURE:
        ( D ) OTHER INFORMATION: Xaa is anywhere from 0 to 35 amino acids ( x i ) SEQUENCE DESCRIPTION: SEQ ID NO: 1:

Ala Asn Phe Leu Val Trp Xaa Glu Ile Val Arg Lys Lys Pro
        5                     10

( 2 ) INFORMATION FOR SEQ ID NO: 2:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i x ) FEATURE:
        ( D ) OTHER INFORMATION: the first Xaa is tryptophan or thioanisolated tryptophan; the second Xaa stands for anywhere from 0 to 35 amino acids ( x i ) SEQUENCE DESCRIPTION: SEQ ID NO: 2:

Ala Asn Phe Leu Val Xaa Xaa Glu Ile Val Arg Lys Lys Pro
        5                     10

( 2 ) INFORMATION FOR SEQ ID NO: 3:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 3:

Ala Asn Phe Leu Val Trp Glu Ile Val Arg Lys Lys Pro
        5                 10

( 2 ) INFORMATION FOR SEQ ID NO: 4:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( i x ) FEATURE:
    ( D ) OTHER INFORMATION: Xaa is tryptophan or thioanisolated tryptophan ( x i ) SEQUENCE DESCRIPTION: SEQ ID NO: 4:

Ala Asn Phe Leu Val Xaa Glu Ile Val Arg Lys Lys Pro
 5                   10

( 2 ) INFORMATION FOR SEQ ID NO: 5:

( i ) SEQUENCE CHARACTERISTICS:
       ( A ) LENGTH: 29 amino acids
       ( B ) TYPE: amino acid
       ( D ) TOPOLOGY: linear ( i i ) MOLECULE TYPE: protein ( i x ) FEATURE:
       ( D ) OTHER INFORMATION: Xaa is tryptophan or thioanisolated tryptophan ( x i ) SEQUENCE DESCRIPTION: SEQ ID NO: 5:

Ala Asn Phe Leu Val Xaa Pro Pro Cys Val Glu Val Gln Leu Arg Pr
 5                   10                  15

Val Gln Val Arg Lys Ile Gly Ile Val Arg Lys Lys Pro
 20                  25

( 2 ) INFORMATION FOR SEQ ID NO: 6:

( i ) SEQUENCE CHARACTERISTICS:
       ( A ) LENGTH: 29 amino acids
       ( B ) TYPE: amino acid
       ( D ) TOPOLOGY: linear ( i i ) MOLECULE TYPE: protein ( x i ) SEQUENCE DESCRIPTION: SEQ ID NO: 6:

Ala Asn Phe Leu Val Trp Pro Pro Cys Val Glu Val Gln Leu Arg Pr
 5                   10                  15

Val Gln Val Arg Lys Ile Gly Ile Val Arg Lys Lys Pro
 20                  25

( 2 ) INFORMATION FOR SEQ ID NO: 7:

( i ) SEQUENCE CHARACTERISTICS:
       ( A ) LENGTH: 125 amino acids
       ( B ) TYPE: amino acid
       ( D ) TOPOLOGY: linear ( i i ) MOLECULE TYPE: protein ( x i ) SEQUENCE DESCRIPTION: SEQ ID NO: 7:

Ser Ile Glu Glu Ala Val Pro Ala Val Cys Lys Thr Arg Thr Val Ile
 5                   10                  15

Tyr Glu Ile Pro Arg Ser Gln Val Asp Pro Thr Ser Ala Asn Phe Leu
 20                  25                  30

Ile Trp Pro Pro Cys Val Glu Val Lys Arg Cys Thr Gly Cys Cys Asn
 35                  40                  45

Thr Ser Ser Val Lys Cys Gln Pro Ser Arg Val His His Arg Ser Val
 50                  55                  60

Lys Val Ala Lys Val Glu Tyr Val Arg Lys Lys Pro Lys Leu Lys Glu
 65                  70                  75                  80

Val Gln Val Arg Leu Glu Glu His Leu Glu Cys Ala Cys Ala Thr Thr
 85                  90                  95

Ser Leu Asn Pro Asp Tyr Arg Glu Glu Asp Thr Gly Arg Pro Arg Glu
 100                 105                 110

```
Ser Gly Lys Lys Arg Lys Arg Lys Arg Leu Lys Pro Thr
115             120                 125
```